(12) United States Patent
Tamori et al.

(10) Patent No.: US 9,090,665 B2
(45) Date of Patent: Jul. 28, 2015

(54) FILLER FOR AFFINITY CHROMATOGRAPHY

(75) Inventors: Kouji Tamori, Minato-ku (JP); Takayoshi Abe, Minato-ku (JP); Yusuke Okano, Minato-ku (JP); Masaki Momiyama, Minato-ku (JP); Hiroshi Kawai, Minato-ku (JP); Satoshi Hyugaji, Minato-ku (JP); Yong Wang, Minato-ku (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 13/638,826

(22) PCT Filed: Mar. 29, 2011

(86) PCT No.: PCT/JP2011/057884
§ 371 (c)(1),
(2), (4) Date: Oct. 1, 2012

(87) PCT Pub. No.: WO2011/125673
PCT Pub. Date: Oct. 13, 2011

(65) Prior Publication Data
US 2013/0023650 A1    Jan. 24, 2013

(30) Foreign Application Priority Data

Mar. 31, 2010 (JP) ................... 2010-081424

(51) Int. Cl.
| | | |
|---|---|---|
| G01N 33/547 | (2006.01) | |
| C07K 1/14 | (2006.01) | |
| G01N 33/545 | (2006.01) | |
| C07K 1/18 | (2006.01) | |
| B01D 15/38 | (2006.01) | |
| C08F 222/10 | (2006.01) | |
| B01J 20/286 | (2006.01) | |
| C07K 1/22 | (2006.01) | |

(52) U.S. Cl.
CPC .............. *C07K 1/18* (2013.01); *B01D 15/3804* (2013.01); *B01D 15/3809* (2013.01); *B01J 20/286* (2013.01); *C08F 222/1006* (2013.01); *C07K 1/22* (2013.01)

(58) Field of Classification Search
CPC ..... C07K 1/22; C08F 220/20; C08F 22/1006; C08F 2200/325; B01D 15/3804; B01D 15/3809
See application file for complete search history.

(56) References Cited

U.S. PATENT DOCUMENTS

| | | | |
|---|---|---|---|
| 4,565,832 A | 1/1986 | Kobashi et al. | |
| 4,772,635 A | 9/1988 | Mitschker et al. | |
| 5,019,270 A | 5/1991 | Afeyan et al. | |
| 5,059,654 A * | 10/1991 | Hou et al. ................ | 525/54.1 |
| 5,064,866 A | 11/1991 | Toyomoto et al. | |
| 5,228,989 A | 7/1993 | Afeyan et al. | |
| 5,384,042 A | 1/1995 | Afeyan et al. | |
| 5,552,041 A | 9/1996 | Afeyan et al. | |
| 5,583,162 A | 12/1996 | Li et al. | |
| 5,605,623 A | 2/1997 | Afeyan et al. | |
| 5,653,922 A | 8/1997 | Li et al. | |
| 5,760,097 A | 6/1998 | Li et al. | |
| 5,833,861 A | 11/1998 | Afeyan et al. | |
| 5,863,957 A | 1/1999 | Li et al. | |
| 6,046,246 A | 4/2000 | Lowe et al. | |
| 6,100,306 A | 8/2000 | Li et al. | |
| 6,482,867 B1 | 11/2002 | Kimura et al. | |
| 2002/0155090 A1 | 10/2002 | Takahashi et al. | |
| 2003/0155300 A1 | 8/2003 | Afeyan et al. | |
| 2005/0043491 A1 | 2/2005 | Mano et al. | |
| 2006/0070950 A1 | 4/2006 | Rasmussen et al. | |
| 2006/0088470 A1 * | 4/2006 | Larsson et al. .............. | 423/702 |
| 2006/0134805 A1 | 6/2006 | Berg et al. | |
| 2007/0207500 A1 | 9/2007 | Bian et al. | |
| 2010/0063261 A1 | 3/2010 | Bian et al. | |
| 2011/0105730 A1 | 5/2011 | Bian et al. | |
| 2011/0262748 A1 | 10/2011 | Tamori et al. | |

FOREIGN PATENT DOCUMENTS

| | | |
|---|---|---|
| EP | 0 006 199 A1 | 1/1980 |
| EP | 0 198 395 A2 | 10/1986 |
| EP | 0 198 395 A3 | 10/1986 |
| GB | 2 184 732 A | 7/1987 |
| JP | 58-32164 A | 2/1983 |
| JP | 58-177140 A | 10/1983 |

(Continued)

OTHER PUBLICATIONS

Svec, Franstisek. Porous polymer monoliths: amazingly wide variety of techniques ennbling their preparation. Journal of Chromatography A, 2010, vol. 1217, pp. 902-924.*

Mateo et al. Immobilizaiton of enzymes on heterofunctional epoxy supports. Nature Protocols 2007, vol. 2, No. 5, pp. 1022-1033.*

(Continued)

*Primary Examiner* — Shafiqul Haq
(74) *Attorney, Agent, or Firm* — Oblon, McClelland, Maier & Neustadt, L.L.P.

(57) ABSTRACT

Provided is a filler for affinity chromatography which is useful for protein purification and contains porous particles that have a high dynamic binding capacity for proteins and excellent pressure characteristics. The filler for affinity chromatography of the present invention is characterized in that it includes a porous particle consisting of a polymer of vinyl monomer including a cross-linkable vinyl monomer that contains hydroxyl group but does not contain epoxy group and an epoxy group-containing non-cross-linkable vinyl monomer, or a cross-linkable vinyl monomer that contains hydroxyl group and epoxy group, ligands bound to the porous particle, and ring-opened epoxy groups.

8 Claims, 4 Drawing Sheets

(56) References Cited

FOREIGN PATENT DOCUMENTS

| | | |
|---|---|---|
| JP | 62-74904 A | 4/1987 |
| JP | 63 159754 | 7/1988 |
| JP | 63 159755 | 7/1988 |
| JP | 63 159756 | 7/1988 |
| JP | 1-112152 A | 4/1989 |
| JP | 2 119937 | 5/1990 |
| JP | 6-340818 A | 12/1994 |
| JP | 7-300509 A | 11/1995 |
| JP | 8 278299 | 10/1996 |
| JP | 10 501173 | 2/1998 |
| JP | 2000 187028 | 7/2000 |
| JP | 2002 239380 | 8/2002 |
| JP | 2003 176363 | 6/2003 |
| JP | 2007-154083 A | 6/2007 |
| JP | 2008 523140 | 7/2008 |
| JP | 2008 232764 | 10/2008 |
| JP | 2011 256176 | 12/2011 |
| WO | 00 77081 | 12/2000 |
| WO | WO 03/029327 A1 | 4/2003 |
| WO | 2006 039455 | 4/2006 |
| WO | WO 2007/013651 A2 | 2/2007 |
| WO | WO 2007/013651 A3 | 2/2007 |

OTHER PUBLICATIONS

Malmsten et al. Immobilization of trypsin on porous glycidyl methacrylate beads: effects of polymer hydrophilization. Colloids and surfaces B: Biointerfaces 2000, vol. 18, pp. 277-284.*

Office Action issued May 21, 2013 in Japanese Patent Application No. 2012-509492 with English language translation.

Extended European Search Report issued Jul. 17, 2013, in European Patent Application No. 11765573.8.

Chen, C-H. et al., "Affinity chromatography of proteins on non-porous copolymerized particles of styrene, methyl methacrylate and glycidyl methacrylate", Journal of Chromatography A, vol. 921, No. 1, pp. 31-37, (2001).

Hatakeyama, M. et al., "Polymer Particles as the Carrier for Affinity Purification", Japanese Journal of Polymer Science and Technology, vol. 64, No. 1, pp. 9-20, (Jan. 2007) (with partial English translation).

International Search Report Issued May 17, 2011 in PCT/JP11/057884 filed Mar. 29, 2011.

Office Action issued Jan. 29, 2013 in Japanese Patent Application No. 2012-509492 with partial English language translation.

* cited by examiner

FIG. 1

(SP4Z)
Number of Amino Acid: 258
Mass: 30181.358 (av.) 30163.051(mono.)

MKHHHHHHPMSDYDIPTTENLYFQGAMVVDNKFNKEQQN

AFYEILHLPNLNEEQRNAFIQSLKDDPSQSANLLAEAKKL

NDAQKEFVDNKFNKEQQNAFYEILHLPNLNEEQRNAFIQS

LKDDPSQSANLLAEAKKLNDAQKELVDNKFNKEQQNAFY

EILHLPNLNEEQRNAFIQSLKDDPSQSANLLAEAKKLNDA

QKKLVDNKFNKEQQNAFYEILHLPNLNEEQRNAFIQSLK

DDPSQSANLLAEAKKLNDAQK

(SPATK)

Number of Amino Acid: 291
MW: 32914.9668 Da

SEQUENCE LISTING

```
<160> NUMBER OF SEQ ID NOS: 15

<210> SEQ ID NO 1
<211> LENGTH: 58
<212> TYPE: PRT
<213> ORGANISM: Staphylococcus aureus
<220> FEATURE:
<223> OTHER INFORMATION: Z domain

<400> SEQUENCE: 1

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 2
<211> LENGTH: 258
<212> TYPE: PRT
<213> ORGANISM: Staphylococcus aureus
<220> FEATURE:
<223> OTHER INFORMATION: SP4Z

<400> SEQUENCE: 2

Met Lys His His His His His His Pro Met Ser Asp Tyr Asp Ile Pro
1               5                   10                  15

Thr Thr Glu Asn Leu Tyr Phe Gln Gly Ala Met Val Val Asp Asn Lys
            20                  25                  30

Phe Asn Lys Glu Gln Gln Asn Ala Phe Tyr Glu Ile Leu His Leu Pro
        35                  40                  45
```

```
Asn Leu Asn Glu Glu Gln Arg Asn Ala Phe Ile Gln Ser Leu Lys Asp
 50                  55                  60

Asp Pro Ser Gln Ser Ala Asn Leu Leu Ala Glu Ala Lys Lys Leu Asn
 65                  70                  75                  80

Asp Ala Gln Lys Glu Phe Val Asp Asn Lys Phe Asn Lys Glu Gln Gln
                 85                  90                  95

Asn Ala Phe Tyr Glu Ile Leu His Leu Pro Asn Leu Asn Glu Glu Gln
                100                 105                 110

Arg Asn Ala Phe Ile Gln Ser Leu Lys Asp Asp Pro Ser Gln Ser Ala
                115                 120                 125

Asn Leu Leu Ala Glu Ala Lys Lys Leu Asn Asp Ala Gln Lys Glu Leu
 130                 135                 140

Val Asp Asn Lys Phe Asn Lys Glu Gln Gln Asn Ala Phe Tyr Glu Ile
145                 150                 155                 160

Leu His Leu Pro Asn Leu Asn Glu Glu Gln Arg Asn Ala Phe Ile Gln
                165                 170                 175

Ser Leu Lys Asp Asp Pro Ser Gln Ser Ala Asn Leu Leu Ala Glu Ala
                180                 185                 190

Lys Lys Leu Asn Asp Ala Gln Lys Leu Val Asp Asn Lys Phe Asn
195                 200                 205

Lys Glu Gln Gln Asn Ala Phe Tyr Glu Ile Leu His Leu Pro Asn Leu
210                 215                 220

Asn Glu Glu Gln Arg Asn Ala Phe Ile Gln Ser Leu Lys Asp Asp Pro
225                 230                 235                 240

Ser Gln Ser Ala Asn Leu Leu Ala Glu Ala Lys Lys Leu Asn Asp Ala
                245                 250                 255

Gln Lys

<210> SEQ ID NO 3
<211> LENGTH: 213
<212> TYPE: DNA
<213> ORGANISM: Staphylococcus aureus
<220> FEATURE:
<223> OTHER INFORMATION: SPZK DNA

<400> SEQUENCE: 3
atgcatcatc atcatcatca cgtgaattcg ctcgaggtgg ataacaaatt caacaaagaa      60
caacaaaatg ctttctatga aatcttacat ttacctaact aaacgaaga acaacgcaat     120 gctttcatcc aaagcctaaa agatgaccca agccaaagcg ctaacctttt agcagaagct     180
aaaaagctaa atgatgcaca aggatctaaa taa                                   213

<210> SEQ ID NO 4
<211> LENGTH: 291
<212> TYPE: PRT
<213> ORGANISM: Staphylococcus aureus
<220> FEATURE:
<223> OTHER INFORMATION: SPATK

<400> SEQUENCE: 4

Met Lys His His His His His His Pro Met Ser Asp Tyr Asp Ile Pro
  1               5                  10                  15

Thr Thr Glu Asn Leu Tyr Phe Gln Gly Ala Met Ala Lys Ala Asp Ala
                 20                  25                  30

Gln Gln Asn Asn Phe Asn Lys Asp Gln Gln Ser Ala Phe Tyr Glu Ile
                 35                  40                  45
```

```
Leu Asn Met Pro Asn Leu Asn Glu Ala Gln Arg Asn Gly Phe Ile Gln
 50                  55                  60

Ser Leu Lys Asp Asp Pro Ser Gln Ser Thr Asn Val Leu Gly Glu Ala
 65                  70                  75                  80

Lys Lys Leu Asn Glu Ser Gln Ala Pro Lys Ala Asp Asn Asn Phe Asn
                 85                  90                  95

Lys Glu Gln Gln Asn Ala Phe Tyr Glu Ile Leu Asn Met Pro Asn Leu
            100                 105                 110

Asn Glu Gln Arg Asn Gly Phe Ile Gln Ser Leu Lys Asp Asp Pro
        115                 120                 125

Ser Gln Ser Ala Asn Leu Leu Ser Glu Ala Lys Lys Leu Asn Glu Ser
130                 135                 140

Gln Ala Pro Lys Ala Asp Asn Lys Phe Asn Lys Glu Gly Ser Ser Gly
145                 150                 155                 160

Lys Ala Asp Ala Gln Gln Asn Asn Phe Asn Lys Asp Gln Gln Ser Ala
                165                 170                 175

Phe Tyr Glu Ile Leu Asn Met Pro Asn Leu Asn Glu Ala Gln Arg Asn
                180                 185                 190

Gly Phe Ile Gln Ser Leu Lys Asp Asp Pro Ser Gln Ser Thr Asn Val
            195                 200                 205

Leu Gly Glu Ala Lys Lys Leu Asn Glu Ser Gln Ala Pro Lys Ala Asp
210                 215                 220

Asn Asn Phe Asn Lys Glu Gln Gln Asn Ala Phe Tyr Glu Ile Leu Asn
225                 230                 235                 240

Met Pro Asn Leu Asn Glu Gln Arg Asn Gly Phe Ile Gln Ser Leu
                245                 250                 255

Lys Asp Asp Pro Ser Gln Ser Ala Asn Leu Leu Ser Glu Ala Lys Lys
            260                 265                 270

Leu Asn Glu Ser Gln Ala Pro Lys Ala Asp Asn Lys Phe Asn Lys Glu
        275                 280                 285

Gly Ser Lys
        290

<210> SEQ ID NO 5
<211> LENGTH: 38
<212> TYPE: DNA
<213> ORGANISM: Artificial
<220> FEATURE:
<223> OTHER INFORMATION: primer containing NcoI cutting site

<400> SEQUENCE: 5
ggaggaccat ggttgtggat aacaaattca acaaagaa                           38

<210> SEQ ID NO 6
<211> LENGTH: 39
<212> TYPE: DNA
<213> ORGANISM: Artificial
<220> FEATURE:
<223> OTHER INFORMATION: primer containing EcoRI cutting site

<400> SEQUENCE: 6
ggtggtgaat tcttttttgtg catcatttag cttttttagc                         39

<210> SEQ ID NO 7
<211> LENGTH: 37
<212> TYPE: DNA
<213> ORGANISM: Artificial
<220> FEATURE:
<223> OTHER INFORMATION: primer containing EcoRI cutting site
```

-continued

<400> SEQUENCE: 7
ggaggagaat tcgtggataa caaattcaac aaagaac                37

<210> SEQ ID NO 8
<211> LENGTH: 36
<212> TYPE: DNA
<213> ORGANISM: Artificial
<220> FEATURE:
<223> OTHER INFORMATION: primer containing SacI cutting site

<400> SEQUENCE: 8
ggtggtgagc tcctattttt gtgcatcatt tagctt                36

<210> SEQ ID NO 9
<211> LENGTH: 33
<212> TYPE: DNA
<213> ORGANISM: Artificial
<220> FEATURE:
<223> OTHER INFORMATION: primer containing SacI cutting site

<400> SEQUENCE: 9
ggtggtgagc tcttttttgtg catcatttag ctt                33

<210> SEQ ID NO 10
<211> LENGTH: 36
<212> TYPE: DNA
<213> ORGANISM: Artificial
<220> FEATURE:
<223> OTHER INFORMATION: primer containing SacI cutting site

<400> SEQUENCE: 10
ggaggagagc tcgtggataa caaattcaac aaagaa                36

<210> SEQ ID NO 11
<211> LENGTH: 39
<212> TYPE: DNA
<213> ORGANISM: Artificial
<220> FEATURE:
<223> OTHER INFORMATION: primer containing HindIII cutting site

<400> SEQUENCE: 11
ggtggtaagc ttttttttgtg catcatttag cttttttagc                39

<210> SEQ ID NO 12
<211> LENGTH: 36
<212> TYPE: DNA
<213> ORGANISM: Artificial
<220> FEATURE:
<223> OTHER INFORMATION: primer containing HindIII cutting site

<400> SEQUENCE: 12
ggaggaaagc ttgtggataa caaattcaac aaagaa                36

<210> SEQ ID NO 13
<211> LENGTH: 36
<212> TYPE: DNA
<213> ORGANISM: Artificial
<220> FEATURE:
<223> OTHER INFORMATION: primer containing XhoI cutting site

<400> SEQUENCE: 13
ggtggtctcg agctattttt gtgcatcatt tagctt                36

```
<210> SEQ ID NO 14
<211> LENGTH: 33
<212> TYPE: DNA
<213> ORGANISM: Artificial
<220> FEATURE:
<223> OTHER INFORMATION: primer containing NcoI cutting site

<400> SEQUENCE: 14
catgccatgg cgaaagctga tgcgcaacaa aat                              33

<210> SEQ ID NO 15
<211> LENGTH: 36
<212> TYPE: DNA
<213> ORGANISM: Artificial
<220> FEATURE:
<223> OTHER INFORMATION: primer containing HindIII cutting site

<400> SEQUENCE: 15
cggggatcct caggcaaagc tgatgcgcaa caaaat                           36
```

FILLER FOR AFFINITY CHROMATOGRAPHY

TECHNICAL FIELD

The present invention relates to a filler for affinity chromatography. More particularly, the present invention relates to a filler for affinity chromatography useful for protein purification, which contains porous particles that have a high dynamic binding capacity for proteins and excellent pressure characteristics.

BACKGROUND ART

Affinity chromatography plays a key role in the research, development and production of proteins including monoclonal antibodies. A filler for affinity chromatography generally contains a solid phase carrier having ligands that selectively bind to target molecules. As the ligands on the solid phase carrier used in affinity chromatography show high selectivity to the target molecules, the affinity chromatography enables economic purification with excellent yield at a high speed, as compared to other chromatographic techniques such as ion-exchange chromatography, gel filtration chromatography, and reverse phase liquid chromatography.

Agarose particle is mainly used for the solid phase carrier for a filler for affinity chromatography (Patent Documents 1 and 2). Due to their high hydrophilicity, the agarose particle shows high ligand activity, and high dynamic binding capacity for the target molecule.

Porous particle consisting of a styrene-divinylbenzene polymer may be used as another solid phase carrier for a filler for affinity chromatography (Patent Documents 3 and 4). The porous particles consisting of a polymer of vinyl monomers such as styrene-divinylbenzene generally shows high elastic modulus and excellent pressure characteristics.

Furthermore, in order to balance high dynamic binding capacity and pressure characteristics in a filler for affinity chromatography, a particle in which sugar chains such as agarose are bound to the fine pores of porous particles consisting of a polymer of a vinyl monomer has been suggested (Patent Document 5).

Meanwhile, there have been the cases in which porous particles consisting of a polymer of a hydroxyl group-containing cross-linkable vinyl monomer is used in chromatography; however, these examples are all suitable only for gel filtration chromatography or reverse phase liquid chromatography for analytical purposes (Patent Documents 6 to 8).

PRIOR ART DOCUMENTS

Patent Document

Patent Document 1: JP-A-2008-523140
Patent Document 2: JP-A-2009-522580
Patent Document 3: JP-A-H08-278299
Patent Document 4: JP-A-H10-501173
Patent Document 5: JP-A-2008-232764
Patent Document 6: JP-A-2002-239380
Patent Document 7: JP-A-2003-176363
Patent Document 8: JP-A-2000-187028

SUMMARY OF THE INVENTION

Problems to be Solved by the Invention

However, since agarose particles generally have low elastic modulus, the pressure of the column disadvantageously increases when medium flows at a high speed, and therefore, the agarose particles have poor pressure characteristics. Furthermore, since agarose particles are generally produced from natural seaweeds via a long and complicated process, the agarose is disadvantageously difficult to obtain particles with constant product quality. Meanwhile, since porous particles consisting of a polymer of a vinyl monomer such as styrene-divinylbenzene have low hydrophilicity, the porous particles impart low ligand activity and the dynamic binding capacity for a target molecule is disadvantageously low. Furthermore, because particles, in which sugar chains such as agarose are bound to the fine pores of porous particles consisting of a polymer of a vinyl monomer, are produced via a long and complicated process as is the case of the agarose particles, such particles have disadvantages that a product having affinity chromatography grade quality is expensive, or products with constant quality are not easily obtained. Further, conventional porous particles consisting of a polymer of a hydroxyl group-containing cross-linkable vinyl monomer, which have been used for gel filtration chromatography or reverse phase chromatography, are not likely to balance high dynamic binding capacity and pressure characteristics required for using as a filler for affinity chromatography.

Thus, an object of the present invention is to provide a filler for affinity chromatography useful for protein purification, which has high dynamic binding capacity for proteins and excellent pressure characteristics.

Means for Solving the Problem

The filler for affinity chromatography related to an embodiment of the present invention contains:
 a porous particle consisting of a polymer of vinyl monomer including
  a cross-linkable vinyl monomer that contains hydroxyl group but does not contain epoxy group and an epoxy group-containing non-cross-linkable vinyl monomer,
  or a cross-linkable vinyl monomer that contains hydroxyl group and epoxy group;
 ligands that is bound to the porous particle; and
 ring-opened epoxy groups.

In regard to the filler for affinity chromatography, the ligand may be protein containing at least one selected from protein A, immunoglobulin-binding domain of protein A, and variant thereof.

In regard to the filler for affinity chromatography, the vinyl monomers may consist of:
 20 to 90 parts by mass of (X-1) a cross-linkable vinyl monomer that contains hydroxyl group but does not contain epoxy group;
 0 to 40 parts by mass of (X-2) a cross-linkable vinyl monomer that contains neither hydroxyl group nor epoxy group;
 1 to 40 parts by mass of (M-1) an epoxy-containing non-cross-linkable vinyl monomer; and
 0 to 70 parts by mass of (M-2) a non-cross-linkable vinyl monomer which does not contain epoxy group (with the proviso that the total amount of (X-1), (X-2), (M-1) and (M-2) is 100 parts by mass).

In regard to the filler for affinity chromatography, the ring-opened epoxy group can be obtained by ring-opening of the epoxy group contained in the polymer by using thioglycerol.

In regard to the filler for affinity chromatography, the porous particle can be obtained by performing suspension polymerization of:
 100 parts by mass of the vinyl monomers, and
 a water-based mixture containing (P-1) as an essential component, wherein the (P-1) is at least one porogen selected from linear, branched or cyclic, C7 to C14 alcohol, ether, aldehyde, ketone and ester, and C8 to C10 alkylbenzene (with the proviso that the total amount of porogens is 100 to 400 parts by mass, and the content of (P-1) is 10% by mass or more in 100% by mass of the total amount of porogens).

In regard to the filler for affinity chromatography, the pore volume of the porous particle obtainable when fine pores having a pore diameter in the range of 10 to 5,000 nm are measured with a mercury porosimeter, may be 1.00 to 1.90 ml/g.

In regard to the filler for affinity chromatography, the particle size of the porous particle may be 35 to 100 μm.

The method for isolating immunoglobulins related to another embodiment of the present invention includes:
a step of using the filler for affinity chromatography described above to adsorb immunoglobulins to the filler; and
a step of eluting the immunoglobulins.

A column relating to another embodiment of the present invention is a packed column for affinity chromatography which is packed with the filler for affinity chromatography described above.

Effects of the Invention

According to the filler for affinity chromatography according to the present invention, a filler for affinity chromatography useful for protein purification, which has high dynamic binding capacity for proteins and also has excellent pressure characteristics, can be provided.

BRIEF DESCRIPTION OF DRAWINGS

FIG. 1 is a diagram illustrating the amino acid sequence of the immunoglobulin binding protein (SP4Z) prepared in Example 1 of the present invention;

DETAILED DESCRIPTION OF THE INVENTION

Figure 2:
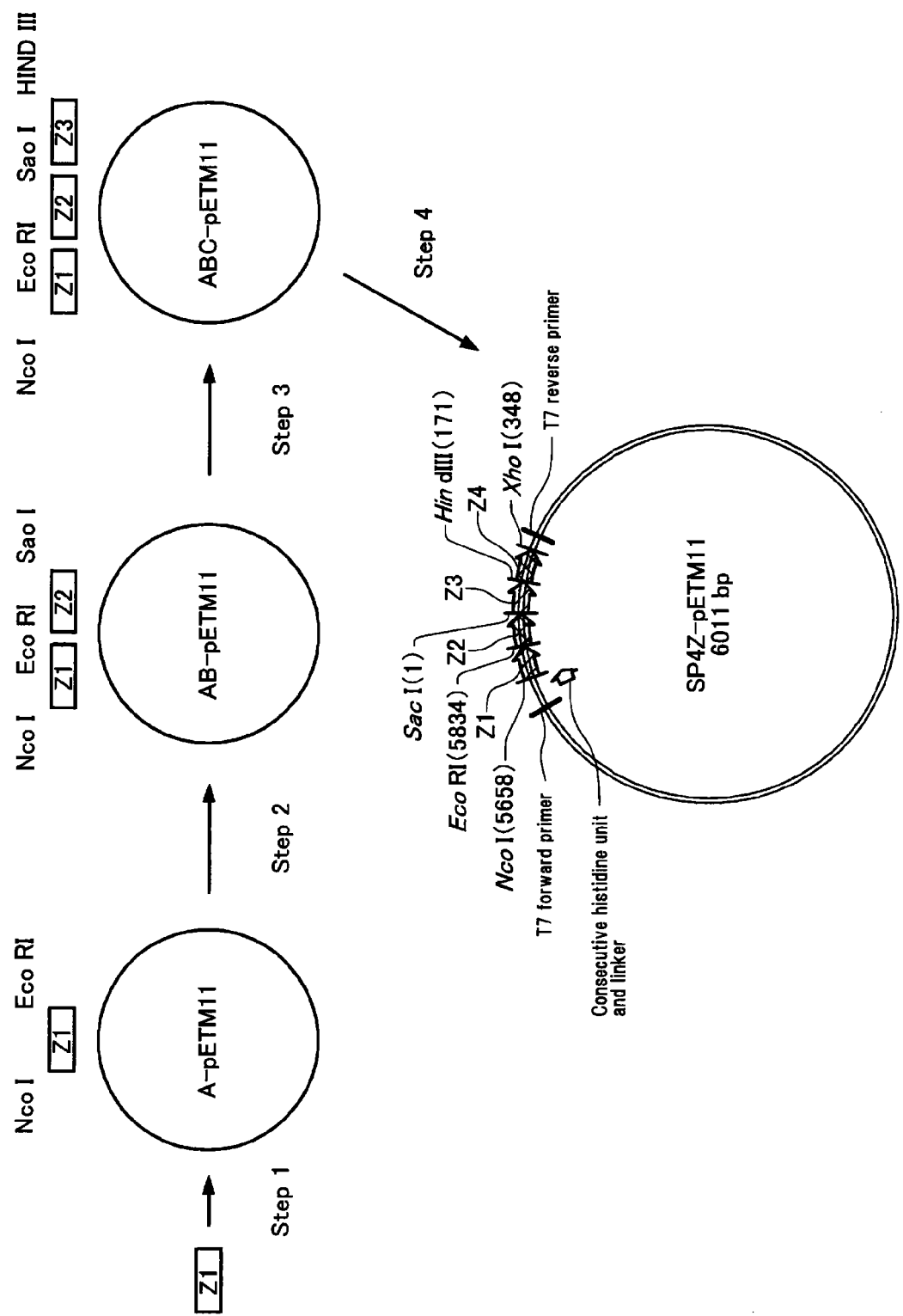
FIG. 2 is a diagram explaining the constitution of a DNA fragment, that encodes the immunoglobulin binding protein of Example 1 of the present invention and is inserted into an expression vector (pETM-11)

Hereinafter, the filler for affinity chromatography of the present invention is explained in more detail.

1. Filler for Affinity Chromatography

The filler for affinity chromatography of the present invention contains
a porous particle consisting of a polymer of vinyl monomer including
a cross-linkable vinyl monomer that contains hydroxyl group but does not contain epoxy group and an epoxy group-containing non-cross-linkable vinyl monomer, or a cross-linkable vinyl monomer that contains hydroxyl group and epoxy group;
ligands that is bound to the porous particles, and
ring-opened epoxy groups.

1.1. Constitution of the Porous Particle

Porous particle that constitutes the filler for affinity chromatography of the present invention is a carrier particle consisting of
a copolymer of vinyl monomer containing, as essential components, a cross-linkable vinyl monomer that contains hydroxyl group but does not contain epoxy group, and an epoxy group-containing non-cross-linkable vinyl monomer;
or a homopolymer of vinyl monomer containing only a cross-linkable vinyl monomer that contains hydroxyl group and epoxy group, as an essential component. Since the polymer contains epoxy groups, the porous particle consisting of the polymer, prior to binding with ligands, contains epoxy groups. The epoxy group content of the porous particle prior to binding with ligands is 0.05 to 4.0 mmol/g.

1.1.1. Cross-Linkable Vinyl Monomer that Contains Hydroxyl Group but does not Contain Epoxy Group The cross-linkable vinyl monomer that contains hydroxyl group but does not contain epoxy group is a cross-linkable monomer which has two or more polymerizable vinyl groups (the group having ethylenically unsaturated bond) and one or more hydroxyl groups per one molecule, but does not have epoxy group. When the porous particle is hydrophilized and controlled to have an appropriate elastic modulus by using the cross-linkable vinyl monomer that contains hydroxyl group but does not contain epoxy group, a filler for affinity chromatography having high dynamic binding capacity for proteins and excellent pressure characteristics can be obtained.

The cross-linkable vinyl monomer that contains hydroxyl group but does not contain epoxy group is preferably an aliphatic polyvinyl monomer, and more preferably a (meth) acrylate of a polyhydric alcohol. Specific examples of the cross-linkable vinyl monomer that contains hydroxyl group but does not contain epoxy group include glycerin di(meth) acrylate, trimethylolethane di(meth)acrylate, trimethylolpropane di(meth)acrylate, butanetriol di(meth)acrylate, pentaerythritol di(meth)acrylate, pentaerythritol tri(meth) acrylate, dipentaerythritol di(meth)acrylate, dipentaerythritol tri(meth)acrylate, dipentaerythritol tetra (meth)acrylate, dipentaerythritol penta(meth)acrylate, inositol di(meth)acrylate, inositol tri(meth)acrylate, and inositol tetra(meth)acrylate. Further examples include disubstituted or higher-substituted (meth)acrylates of various saccharides such as glucose di(meth)acrylate, glucose tri(meth)acrylate, glucose tetra(meth)acrylate, mannitol di(meth)acrylate, mannitol tri(meth)acrylate, mannitol tetra(meth)acrylate, and mannitol penta(meth)acrylate. Still further examples include hydroxyl group-containing cross-linkable vinyl monomers having a structure similar to that of a dehydration condensation reaction product of (meth)acrylic acid and a polyhydric amino alcohol such as diaminopropanol, tris(hydroxymethyl) aminomethane or glucosamine.

Particularly preferred examples of the cross-linkable vinyl monomer that contains hydroxyl group but does not contain epoxy group include glycerin di(meth)acrylate, pentaerythritol tri(meth)acrylate, and inositol tri(meth)acrylate; and most preferred examples thereof include glycerin di(meth)acrylate. When alkali resistance is considered, methacrylates, acrylamides, and methacrylamides are preferred. In view of alkali resistance, the cross-linkable vinyl monomer that contains hydroxyl group but does not contain epoxy group is particularly preferably glycerin dimethacrylate, pentaerythritol trimethacrylate, or inositol trimethacrylate, and is most preferably glycerin dimethacrylate.

1.1.2. Epoxy Group-Containing Non-Cross-Linkable Vinyl Monomer

The epoxy group-containing non-cross-linkable vinyl monomer is a non-cross-linkable monomer having one polymerizable vinyl group and one or more epoxy groups in one molecule. The number of epoxy groups carried by the epoxy group-containing non-cross-linkable vinyl monomer is preferably 1 to 3 per molecule, and more preferably one. The epoxy group-containing non-cross-linkable vinyl monomer is an essential component for introducing an appropriate amount of epoxy groups prior to the binding of a ligand to the porous particle, which is obtainable by using a copolymer of vinyl monomers including a cross-linkable vinyl monomer that contains hydroxyl group but does not contain epoxy group, and an epoxy group-containing non-cross-linkable vinyl monomer.

As the epoxy group-containing non-cross-linkable vinyl monomer, a non-cross-linkable monomer having one polymerizable vinyl group and one epoxy group in one molecule is easily available by industrial process. Examples of such an epoxy group-containing non-cross-linkable vinyl monomer include (meth)acrylic acid esters such as glycidyl(meth)acrylate, 4-hydroxybutyl(meth)acrylate glycidyl ether, 3,4-epoxycyclohexylmethyl(meth)acrylate, and α-(meth)acryl-ω-glycidyl polyethylene glycol; aromatic vinyl compounds such as vinylbenzyl glycidyl ether; allyl glycidyl ether, 3,4-epoxy-1-butene, and 3,4-epoxy-3-methyl-1-butene. Glycidyl (meth)acrylate and 4-hydroxybutyl(meth)acrylate glycidyl ether are particularly preferred.

In addition to the above, a cross-linkable vinyl monomer that contains hydroxyl group and epoxy group can be used alone as a vinyl monomer, instead of the cross-linkable vinyl monomer that contains hydroxyl group but does not contain epoxy group and the epoxy group-containing non-cross-linkable vinyl monomer. Examples of the cross-linkable vinyl monomer that contains hydroxyl group and epoxy group include pentaerythritol di(meth)acrylate glycidyl ether, inositol di(meth)acrylate glycidyl ether, and inositol tri(meth)acrylate glycidyl ether. Meanwhile, the cross-linkable vinyl monomer that contains hydroxyl group and epoxy group may also be used together with the cross-linkable vinyl monomer that contains hydroxyl group but does not contain an epoxy group and the epoxy group-containing non-cross-linkable vinyl monomer, described above.

1.1.3. Preferred Vinyl Monomers

The vinyl monomers preferably consist of:
20 to 90 parts by mass of (X-1) a cross-linkable vinyl monomer that contains hydroxyl group but does not contain epoxy group,
0 to 40 parts by mass of (X-2) a cross-linkable vinyl monomer that contains neither hydroxyl group nor epoxy group,
1 to 40 parts by mass of (M-1) an epoxy group-containing non-cross-linkable vinyl monomer, and
0 to 70 parts by mass of (M-2) a non-cross-linkable vinyl monomer that does not contain epoxy group (with the proviso that the total amount of (X-1), (X-2), (M-1) and (M-2) is 100 parts by mass).

Specific examples and suitable examples of the (X-1) cross-linkable vinyl monomer that contains hydroxyl group but does not contain epoxy group are the same as those listed in section 1.1.1. "Cross-linkable vinyl monomer that contains hydroxyl group but does not contain epoxy group". The content of (X-1) is preferably 20 to 90 parts by mass, more preferably 25 to 85 parts by mass, and most preferably 30 to 80 parts by mass. When the content of the (X-1) cross-linkable vinyl monomer that contains hydroxyl group but does not contain epoxy group is from 20 parts by mass to 90 parts by mass, excellent dynamic binding capacity for proteins is provided.

The (X-2) cross-linkable vinyl monomer that contains neither hydroxyl group nor epoxy group is a cross-linkable monomer which has two or more polymerizable vinyl groups per one molecule but has neither hydroxyl group nor epoxy group. The (X-2) cross-linkable vinyl monomer that contains neither hydroxyl group nor epoxy group is used to supplement the (X-1) cross-linkable vinyl monomer that contains hydroxyl group but does not contain epoxy group, and the pressure characteristics may be improved by controlling the elastic modulus to an appropriate value. Suitable examples of the (X-2) cross-linkable vinyl monomer that contains neither hydroxyl group nor epoxy group include an aromatic polyvinyl monomer and an aliphatic polyvinyl monomer, and the aromatic polyvinyl monomer is preferably divinylbenzene. The aliphatic polyvinyl monomer is preferably a polyvalent (meth)acrylate compound. Examples of the polyvalent(meth) acrylate include ethylene glycol di(meth)acrylate, diethylene glycol di(meth)acrylate, triethylene glycol di(meth)acrylate, tetraethylene glycol di(meth)acrylate, propylene glycol di(meth)acrylate, dipropylene glycol di(meth)acrylate, tripropylene glycol di(meth)acrylate, tetrapropylene glycol di(meth)acrylate, 1,4-butanediol di(meth)acrylate, 1,6-hexanediol di(meth)acrylate, trimethylolpropane tri(meth)acrylate, and pentaerythritol tetra(meth)acrylate. Particularly preferred examples include trimethylolpropane trimethacrylate and pentaerythritol tetraacrylate. The content of the (X-2) cross-linkable vinyl monomer that contains neither hydroxyl group nor epoxy group is preferably 0 to 40 parts by mass, and more preferably 0 to 20 parts by mass. When the content of (X-2) is greater than 40 parts by mass, the dynamic binding capacity for proteins may be lowered.

The (X-1) cross-linkable vinyl monomer that contains hydroxyl group but does not contain epoxy group and the (X-2) cross-linkable vinyl monomer that contains neither hydroxyl group nor epoxy group may be industrially available as mixtures, and within the scope of the present invention, these mixtures may be used as supplied.

Specific examples and suitable examples of the (M-1) epoxy group-containing non-cross-linkable vinyl monomer are the same as those listed in section 1.1.2. "Epoxy group-containing non-cross-linkable vinyl monomer". The (M-1) epoxy group-containing non-cross-linkable vinyl monomer is preferably 1 to 40 parts by mass, more preferably 2 to 30 parts by mass, and most preferably 3 to 15 parts by mass. When the content of the (M-1) epoxy group-containing non-cross-linkable vinyl monomer is from 1 part by mass to 40 parts by mass, an appropriate amount of epoxy groups may be contained in the porous particle formed of a polymer thus obtainable.

The (M-2) non-cross-linkable vinyl monomer that does not contain epoxy group is preferably a hydrophilic vinyl monomer, and more preferably a non-cross-linkable vinyl monomer that contains hydroxyl group. When a hydrophilic monomer is used as the (M-2) non-cross-linkable vinyl monomer that does not contain epoxy group, hydrophilicity of the filler for affinity chromatography may be enhanced, and a high dynamic binding capacity for a target molecule can be exhibited. Among hydrophilic vinyl monomers, examples of a hydrophilic vinyl monomer that does not contain hydroxyl group and is non-cross-linkable include dimethylacrylamide, acryloylmorpholine, methoxyethyl(meth)acrylate, diacetone (meth)acrylamide, and N-vinyl-2-pyrrolidone. Examples of a vinyl monomer that contains hydroxyl group but is non-cross-linkable include glycerol mono(meth)acrylate, trimethylolethane mono(meth)acrylate, trimethylolpropane mono(meth) acrylate, butanetriol mono(meth)acrylate, pentaerythritol mono(meth)acrylate, dipentaerythritol mono(meth)acrylate, inositol mono(meth)acrylate, hydroxyethyl(meth)acrylate, and hydroxyethyl(meth)acrylamide. Preferred examples include glycerol monomethacrylate, hydroxyethyl methacrylate, hydroxyethyl acrylamide, and polyethylene glycol (meth)acryl ester, while glycerol monomethacrylate is most preferred. The content of the (M-2) non-cross-linkable vinyl monomer that does not contain epoxy group is preferably 0 to 70 parts by mass, and more preferably greater than 0 parts by mass and less than or equal to 40 parts by mass. When the content of (M-2) is larger than 70 parts by mass, poor pressure characteristics may be obtained.

Specific examples of a suitable amount ratio for preferred vinyl monomers include:

a vinyl monomer consisting of:

25 to 85 parts by mass of (X-1) a cross-linkable vinyl monomer that contains hydroxyl group but does not contain epoxy group;

0 to 20 parts by mass of (X-2) a cross-linkable vinyl monomer that contains neither hydroxyl group nor epoxy group;

2 to 30 parts by mass of (M-1) an epoxy group-containing non-cross-linkable vinyl monomer; and 0 to 70 parts by mass of (M-2) a non-cross-linkable vinyl monomer that does not contain epoxy group, or a vinyl monomer consisting of:

30 to 80 parts by mass of (X-1) a cross-linkable vinyl monomer that contains hydroxyl group but does not contain epoxy group;

0 to 20 parts by mass of (X-2) a cross-linkable vinyl monomer that contains neither hydroxyl group nor epoxy group;

3 to 15 parts by mass of (M-1) an epoxy group-containing non-cross-linkable vinyl monomer; and more than 0 parts by mass but not less than 40 parts by mass of (M-2) a non-cross-linkable vinyl monomer that does not contain epoxy group, with the proviso that, in any specific example of a vinyl monomer, total amount of (X-1), (X-2), (M-1), and (M-2) is 100 parts by mass.

1.1.4. Production of Porous Particle

The porous particle can be produced by, for example, seed polymerization, suspension polymerization, which are well known in the art. The two-stage swelling polymerization method disclosed in JP-B-57-24369 may be suitably used as the seed polymerization method. During the polymerization, in addition to the above monomers, water and porogens are used as essential components, and, for example, a polymerization initiator, a polymer dispersant, a surfactant, a salt, seed particles, a water-soluble polymerization inhibitor are used as necessary.

A preferred polymerization method in the production of the porous particle is suspension polymerization method using a water-based mixture which contains, as essential components, 100 parts by mass of the vinyl monomer described above, and (P-1) at least one porogen selected from linear, branched or cyclic, C7 to C14 alcohol, ether, aldehyde, ketone and ester, and C8 to C10 alkylbenzene.

(P-2), porogen other than (P-1), may also be used in combination. The amount of the porogens used is preferably 100 to 400 parts by mass in total relative to 100 parts by mass of the monomer. The amount of (P-1) used is preferably 10% by mass or more in 100% by mass of the total amount of the porogens.

Specific examples of the porogen (P-1) include:

as alcohols, 1-heptanol, 2-heptanol, 3-heptanol, 4-heptanol, 2,4-dimethyl-3-pentanol, 5-methyl-2-hexanol, 2-ethyl-1-hexanol, 2-octanol, 3-octanol, 5-methyl-3-heptanol, 1-nonanol, and 3,5,5-trimethylhexanol;

as ethers, hexyl methyl ether, dibutyl ether, and cineole;

as aldehydes, heptanal, octanal, 2-ethyl-1-hexanal, nonanal, 3,5,5-trimethylhexanal, 1-decanal, and dodecanal;

as ketones, 2-heptanone, 3-heptanone, 4-heptanone, 2,4-dimethyl-3-pentanone, 4,4-dimethyl-2-pentanone, 5-methyl-2-hexanone, 2-octanone, 3-octanone, 5-methyl-3-heptanone, 2,6-dimethyl-4-heptanone, 2-nonanone, 3-nonanone, 4-nonanone, 3,3,5-trimethylcyclohexanone, 2-decanone, 3-decanone, 2-undecanone, 4-t-pentylcyclohexanone, 2-hexylcyclopentanone, 2-heptylcyclopentanone, and dicyclohexyl ketone;

as esters, hexyl formate, pentyl acetate, isopentyl acetate, butyl propionate, isobutyl propionate, propyl butyrate, isopropyl butyrate, propyl isobutyrate, isopropyl isobutyrate, ethyl valerate, ethyl isovalerate, ethyl pivalate, methyl hexanoate, hexyl acetate, cyclohexyl acetate, 2-ethylbutyl acetate, isopentyl propionate, butyl butyrate, butyl isobutyrate, isobutyl butyrate, isobutyl isobutyrate, propyl valerate, propyl isovalerate, ethyl hexanoate, methyl heptanoate, heptyl acetate, hexyl propionate, pentyl butyrate, isopenyl butyrate, pentyl isobutyrate, isopentyl isobutyrate, isobutyl valerate, propyl hexanoate, isopropyl hexanoate, ethyl heptanoate, methyl octanoate, octyl acetate, isooctyl acetate, 2-ethylhexyl acetate, hexyl butyrate, cyclohexyl butyrate, pentyl valerate, isopentyl isovalerate, butyl hexanoate, isobutyl hexanoate, ethyl octanoate, methyl nonanoate, nonyl acetate, pentyl hexanoate, ethyl nonanoate, propyl 2-ethylhexanoate, ethyl 3,5,5-trimethylhexanoate, methyl decanoate, δ-dodecanolactone, decyl acetate, ethyl decanoate, citronellyl acetate, methyl dodecanoate, dodecyl acetate, and ethyl dodecanoate; and as alkylbenzenes, xylene, ethylbenzene, cumene, n-propylbenzene, n-butylbenzene, t-butylbenzene, sec-butylbenzene, isobutylbenzene, ethyltoluene, cymene, and mesitylene.

From the viewpoint of maintaining the ligand activity at a high level without inhibiting hydrophilicity, the porogen of (P-1) is preferably alcohol, ether, aldehyde, ketone, or ester, and more preferably ketone or ester. C7 to C10 ketone and ester are most preferred.

The (P-2) is porogen other than (P-1), and is a component which may be added to adjust the pore volume of the porous particle. The solubility of (P-2) in water at 20° C. is preferably 200 or less.

If the (P-2) porogens of less than C7 linear or branched alcohols, ethers, aldehydes, ketones and esters, and less than C8 alkylbenzenes are contained as main components in composition, a large pore diameter that is suitable for protein isolation or the like may not be obtained, and the pore volume may become small. If more than C14 alcohols, ethers, aldehydes, ketones and esters, and more than C10 alkylbenzenes are used as main components, the pore volume may become small, or non-porous fine particles may be formed.

The total amount of the porogens including (P-1) is usually 100 to 400 parts by mass, and preferably 150 to 300 parts by mass, relative to 100 parts by mass of the monomer mixture. If the total amount of the porogens is less than 100 parts by mass, a large pore diameter suitable for, for example, protein isolation, may not be obtained, and the pore volume may become small. If the total amount of the porogens is more than 400 parts by mass, the pore volume may become excessively large, or non-porous fine particles may be formed.

The amount of (P-1) is preferably 10% by mass or more compared to the total amount of porogens, and more preferably 20% by mass or more. When the total amount of (P-1) is less than 10% by mass of the total amount of porogens, the pore volume may become small.

The polymerization solvent for suspension polymerization is water. An organic solvent such as alcohol may be incorporated to the extent that the effect of the present invention is not impaired. The amount of water is preferably 200 to 10,000 parts by mass, and more preferably 500 to 5,000 parts by mass, relative to 100 parts of the total amount of the monomers. When the amount of water is within the above range, association between the particles during polymerization is inhibited, so that the particle size is easily controlled, and excellent productivity is obtained.

Examples of the polymerization initiator that may be used include water-soluble initiators, including persulfates such as potassium persulfate, sodium persulfate and ammonium persulfate, hydrogen peroxide, t-butyl hydroperoxide, t-butyl peroxymaleic acid, succinic acid peroxide, and 2,2'-azobis[2-N-benzylamidino]propane hydrochloride; oil-soluble initiators such as benzoyl peroxide, lauroyl peroxide, cumene hydroperoxide, diisopropylperoxydicarbonate, cumyl peroxyneodecanoate, cumyl peroxyoctanoate, t-butyl peroxy-2-ethylhexanoate, 3,5,5-trimethylhexanoyl peroxide, azobisisobutyronitrile, and azobisisovaleronitrile; and redox-based initiators using both an organic peroxide and a reducing agent such as sodium sulfite, rongalite, and sodium ascorbate. The polymerization initiator is preferably an oil-soluble initiator or an oil-soluble redox initiator, and from the view point of productivity, the polymerization initiator is more preferably an oil-soluble initiator. The amount of the initiator is preferably 0.01 to 10 parts by mass, and more preferably 0.05 to 5 parts by mass, relative to 100 parts by weight of the total amount of the monomers. These polymerization initiators may be supplied to a polymerization system after being dissolved in water, a monomer mixture, or a porogen, or may also be added to a polymerization system at room temperature or under heating alone. When an initiator exhibiting acidity or basicity such as a persulfate is used during polymerization and hydrolysis of epoxy group is necessary to be prevented, it is preferable to carry out suspension polymerization in a buffer solution in which a near neutral pH is maintained. It is also possible to carry out suspension polymerization without using an initiator, by using ultraviolet radiation or an electron beam, and a known photoradical initiator can also be used.

As the polymer dispersant, a water-soluble polymer such as a polyvinyl alcohol having a degree of saponification of 80% to 95%, or polyvinylpyrrolidone, can be used.

As the surfactant, anionic surfactants such as sodium dodecyl sulfate, sodium dodecyl benzenesulfonate, and polyoxyethylene dodecyl ether sulfuric acid ester salt; and nonionic surfactants such as polyoxyethylene alkyl ether can be used.

As the salt, sodium chloride, sodium sulfate, sodium carbonate and the like can be suitably used.

As the seed particles, polystyrene particles, polyalkyl (meth)acrylate particles and the like, each having a weight average molecular weight of about 1,000 to 100,000, can be used.

As the water-soluble polymerization inhibitor, iodides such as potassium iodide, nitrites such as sodium nitrite, thiosulfates such as sodium thiosulfate, and water-soluble quinone compounds such as sulfonated naphthohydroquinone ammonium salt can be suitably used.

In the process of seed polymerization, porous particle having a particle size that is essential to the filler for affinity chromatography of the present invention can be obtained by adjusting the size and amount of the seed particles, the amount of the monomers, and the amount of the porogen. In the process of suspension polymerization, porous particles having a particle size that is essential to the filler for affinity chromatography of the present invention can be obtained by adjusting the type and amount of the polymer dispersant and the surfactant, the stirring speed, the stirring blade, and the shape and size of the polymerization vessel.

It is known that the pore volume of the porous particles can be adjusted by changing the ratio of the monomers and the porogen. In addition, the pore volume of the porous particles can be adjusted by changing, for example, the type and amount of the salt or polymerization inhibitor used at the time of polymerization, the polymerization temperature. The pore volume of the porous particles as a filler for affinity chromatography can be adjusted by changing the pore volume of the porous particles prior to ligand binding, and the amount of the ligand to be bound.

The temperature and time required for polymerization are, in the case of using an initiator other than a redox-based initiator, preferably 30 min to 24 hours at 40° C. to 100° C., and more preferably 1 to 10 hours at 60° C. to 90° C.

After the completion of polymerization, it is preferable to wash the porous particles with a good solvent for the seed particles and/or the porogen, from the viewpoint that the binding of a ligand that will be described below is facilitated. For example, acetone, ethanol, isopropyl alcohol can be suitably used as a washing solvent. Furthermore, if necessary, the porous particles may be dispersed by using, for example, an ultrasonic disperser, before or after washing. Further, it is preferable to remove small particles or coarse particles by methods such as decantation and filtration, from the viewpoint of improving the pressure characteristics or improving the dynamic binding capacity for proteins.

1.1.5. Epoxy Group Content

The epoxy group contained in the porous particles prior to ligand binding is a functional group for binding a ligand, and is also a functional group that serves as a source for hydrophilicity enhancement as the filler for affinity chromatography after ring-opening. The epoxy group content prior to ligand binding is 0.05 to 4.0 mmol/g, preferably 0.08 to 2.5 mmol/g, and more preferably 0.10 to 1.5 mmol/g. When the epoxy group content prior to ligand binding is 0.05 mmol/g or more, suitable amount of the ligand binding is obtained, and a decrease of the dynamic binding capacity for proteins is prevented. Furthermore, when the epoxy group content prior to ligand binding is 4.0 mmol/g or less, a decrease of the ligand activity during storage is prevented, accordingly, a decrease of the dynamic binding capacity for proteins is also prevented. The epoxy group content of the porous particles prior to ligand binding can be quantitatively determined by the steps of: adding an excess amount of hydrochloric acid to the porous particles for ring-opening the epoxy groups by addition reaction with hydrochloric acid; neutralizing the remaining hydrochloric acid with an excess amount of an aqueous sodium hydroxide solution; and then performing back-titration of the remaining sodium hydroxide with hydrochloric acid. The epoxy group content of the porous particles prior to ligand binding can be adjusted by, for example, the amount of the epoxy group-containing vinyl monomer, the

1.2. Constitution of Filler for Affinity Chromatography

The filler for affinity chromatography of the present invention contains the porous particle, the ligands bound to the porous particle, and ring-opened epoxy groups.

One embodiment of the filler for affinity chromatography contains ligand-bound porous particle having ring-opened epoxy groups, which is obtained by binding the ligand to the porous particle formed of the polymer specifically described above, and opening the epoxy ring groups contained in the polymer.

The volume average particle size of the ligand-bound porous particle is preferably 35 to 100 μm. Further, the pore volume obtainable when fine pores having a pore diameter in the range of 10 to 5,000 nm are measured using a mercury porosimeter, is preferably 1.00 to 1.90 ml/g.

1.2.1. Ligand

The type of the ligand is not particularly limited as long as the ligand has appropriate affinity to the target molecule. For example, proteins such as protein A, protein G and avidin; peptides such as insulin; antibodies such as monoclonal antibodies; enzymes; hormones; DNA; RNA; carbohydrates such as heparin, Lewis X, and ganglioside; and low molecular weight compounds such as iminodiacetic acid, synthetic dyes, 2-aminophenylboronic acid, 4-aminobenzamidine, glutathione, biotin, and derivatives thereof, can be used. The above exemplified ligands may be used as a whole molecule, alternatively, the fragments thereof obtainable by, for example, recombination, enzyme treatments may also be used. Artificially synthesized peptides or peptide derivatives may also be used.

Examples of a ligand suitable for the separation or purification of immunoglobulins include protein A and protein G, more preferred examples include an immunoglobulin-binding domain of protein A, and the most preferred examples include a protein in which a peptide containing four or more consecutive histidine units is added to a terminal of an immunoglobulin-binding domain of protein A. Examples of such a protein include immunoglobulin binding proteins represented by the following formula (1) or formula (2).

The term "protein" in the present invention means any molecule having peptide structural unit, and conceptually including, for example, partial fragments of wild type proteins, and variants obtained by artificially modifying the amino acid sequences of wild type proteins. Furthermore, an "immunoglobulin-binding domain" means a functional unit of a polypeptide having an immunoglobulin-binding activity by itself, and an "immunoglobulin-binding protein" means a protein which has specific affinity to an immunoglobulin and includes the "immunoglobulin-binding domain." The term "immunoglobulin binding" means binding to a region other than the complementarity determining region (CDR) of an immunoglobulin molecule, particularly binding to the Fc fragment. The term "ligand" used in relation to affinity chromatography in the present invention represents a part which binds to a target substance for affinity chromatography.

1.2.2. Immunoglobulin-Binding Domain

The immunoglobulin-binding domain of protein A may be a wild type immunoglobulin-binding domain or a recombinant type immunoglobulin-binding domain. The immunoglobulin-binding domain of protein A is preferably at least one immunoglobulin-binding domain selected from the group consisting of an A domain, a B domain, a C domain, a D domain, an E domain, and a Z domain. The amino acid sequences of the A domain, the B domain, the C domain, the D domain, the E domain, and the Z domain are disclosed in FIG. 1 of Moks T, Abrahms L, et al., Staphylococcal protein A consists of five IgG-binding domains, Eur J Biochem. 1986, 156, 637-643. The disclosure of the above document is incorporated herein by reference. A protein which consists of an amino acid sequence having an identity of 70% or more (preferably 90% or more) with the amino acid sequence of each domain disclosed in the above document may also be used as an immunoglobulin-binding domain of protein A of the present invention.

The recombinant immunoglobulin-binding domain is considered to have an immunoglobulin activity equal to that of non-recombinant immunoglobulin-binding domain. For example, the amino acid sequence of the recombinant immunoglobulin-binding domain preferably has an identity of 70% or more (preferably 90% or more) with the amino acid sequence of wild type immunoglobulin-binding domain of protein A. Specific examples of the recombinant immunoglobulin-binding domain include the Z domain (SEQ ID NO: 1) disclosed in Nilsson B. et al., Protein engineering, 1987, vol. 1, No. 2, pp. 107 to 113, and the alkali-resistant mutant Z domain disclosed in US 2006/0194955A1 (Hober et al.).

The ligand used for the filler for affinity chromatography may have plural immunoglobulin-binding domains that may be the same or different from each other.

For example, the ligand may have, as an immunoglobulin-binding domain of protein A, (D domain–A domain)n (herein, n represents an integer of at least 1 (preferably 1 to 6), and there may be an optional amino acid sequence between the D domain and the A domain), that is, it may contain a repeating unit containing A domain and D domain. Furthermore, because the filler for affinity chromatography of the present invention has opportunity of contacting with an aqueous alkali solution during use, the ligand may have a repeating unit which contains the Z domain of protein A.

Furthermore, in the present invention, the ligand may contain one or more of the above each domain, or fragment or mutant thereof.

In the present invention, a fragment of an immunoglobulin-binding domain refers to the fragment having a part of an amino acid sequence of the corresponding domain and having an immunoglobulin binding activity. Preferably, the fragment of an immunoglobulin-binding domain refers to the fragment having sequence identity of 90% or more, and more preferably 95% or more, with the amino acid sequence of the corresponding domain and having an immunoglobulin binding activity. Furthermore, in the present invention, a variant of an immunoglobulin-binding domain refers to the domain having a sequence identity of 90% or more, and more preferably 95% or more with the amino acid sequence of the corresponding domain and having an immunoglobulin binding activity.

The immunoglobulin-binding domain may contain at least one selected from, for example, Z domain, or fragment or mutant thereof. The Z domain is described in Nilsson B. et al., Protein engineering, 1987, vol. 1, No. 2, pp. 107 to 113.

Furthermore, according to the present invention, the ligand may contain one or more (preferably 4 to 10) Z domain, or fragment or mutant thereof.

Examples of the mutant Z domain include the proteins having the sequence disclosed in JP 4391830 B1. In Claim 1 of JP 4391830 B1, for example, a protein which contains two or more repeating units defined by SEQ ID NO: 1 (that is, Z domain) and has a threonine residue as the 23$^{rd}$ amino acid residue is disclosed.

A fragment of the Z domain (that is, Z fragment) indicates a fragment having a part of the amino acid sequence of Z domain, preferably having a sequence identity of 90% or more, and more preferably 95% or more, with the amino acid sequence of Z domain, and having an immunoglobulin binding activity. Furthermore, a mutant Z domain indicates those having a sequence identity of 90% or more, and more preferably 95% or more, with the amino acid sequence of the Z domain, and an immunoglobulin binding activity. The mutant Z domain preferably shows improved alkali resistance compared to the Z domain. In this regard, alkali resistance of the mutant of Z domain compared to the Z domain can be determined based on the method described in the examples described later.

1.2.3. Immunoglobulin Binding Protein 1

An immunoglobulin binding protein preferred as the ligand is represented by the following formula (1) (hereinafter referred to as "protein 1").

$$R—R^2 \quad (1)$$

(wherein R represents an amino acid sequence consisting of 4 to 300 amino acids and containing a site of 4 to 20 consecutive histidine residues, and $R^2$ represents an amino acid sequence consisting of 50 to 500 amino acids and containing at least one immunoglobulin-binding domain of protein A (wherein the terminal at which $R^2$ binds to R is either C terminal or N terminal of the immunoglobulin-binding domain)).

The number of amino acids included in the amino acid sequence represented by R in the formula (1) is preferably 8 to 100, and the number of histidine residues included in the site including consecutive histidine residues included in R is preferably 4 to 8. The number of amino acids included in the amino acid sequence represented by $R^2$ in the formula (1) is preferably 120 to 480.

It is preferable that either or both of the amino acid sequence represented by R and the amino acid sequence represented by $R^2$ in the formula (1) include a domain t, which consists of 1 to 50 amino acids and contains one amino acid selected from lysine, arginine, and cysteine. In this case, the amino acid sequence may contain plural, the same or different domain t.

Furthermore, R— in the formula (1) is preferably a group represented by the following formula (2)

$$R^1\text{-}r\text{-} \quad (2)$$

(wherein $R^1$ represents an amino acid sequence consisting of 4 to 100 amino acids and containing a site of 4 to 20 consecutive histidine residues (with the proviso that, in $R^1$, the site of consecutive histidine residues binds to r via its terminal), and r represents an arbitrary amino acid sequence consisting of 7 to 200 amino acids).

The number of amino acids included in the amino acid sequence represented by $R^1$ in the formula (2) is preferably 4 to 25, and the number of histidine residues included in the site including consecutive histidine residues in the amino acid sequence represented by $R^1$ is preferably 4 to 8. The number of amino acids included in the amino acid sequence represented by r is preferably 10 to 50.

The amino acid sequence represented by r in the formula (2) may include a TEV domain. When the TEV domain is included in the amino acid sequence represented by r, R and $R^2$ can be separated by the TEV protease. Moreover, the TEV domain is a preferable sequence for obtaining the effects of the present invention (that is, an increase in the amount of immobilization on a carrier, and an increase in immunoglobulin retention capability of the carrier). The amino acid sequence represented by r may include a mutant TEV domain that has an identity of 70% or more, and preferably 90% or more, with the amino acid sequence of the TEV domain (irrespective of whether or not it can be cleaved by TEV protease).

The total number of amino acids which constitute the protein 1 used in the present invention is preferably 54 to 800, and more preferably 80 to 600 when the protein 1 is used for binding to the particles.

1.2.4. Immunoglobulin Binding Protein 2

The ligand may be an immunoglobulin binding protein having alkali resistance. Other examples of the immunoglobulin binding protein, which is preferred as an immunoglobulin binding protein having alkali resistance (hereinafter may be referred to as "protein 2"), is represented by the following formula (3)

$$R—R^2 \quad (3)$$

(wherein R represents an amino acid sequence consisting of 4 to 300 amino acids and containing a site of 4 to 20 consecutive histidine residues, and $R^2$ represents an amino acid sequence consisting of 50 to 500 amino acids and includes Z domain, or fragment or variant thereof, which can bind to an immunoglobulin (wherein the terminal at which $R^2$ binds to R is C terminal or N terminal of an immunoglobulin-binding domain)).

The number of amino acids included in the amino acid sequence represented by R in the formula (3) is preferably 8 to 100, and the number of histidine residues included in the site including consecutive histidine residues in R is preferably 4 to 8. The number of amino acids included in the amino acid sequence represented by $R^2$ in the formula (1) is preferably 120 to 480.

Furthermore, R— in the formula (3) is preferably a group represented by the following formula (4)

$$R^1\text{-}r\text{-} \quad (4)$$

(wherein $R^1$ represents an amino acid sequence consisting of 4 to 100 amino acids and containing a site of 4 to 20 consecutive histidine residues (with the proviso that, the site of 4 to 20 consecutive histidine residues binds to r via its terminal), and r represents an arbitrary amino acid sequence that includes 7 to 200 amino acids).

Furthermore, similar to the formula (2), the amino acid sequence represented by r in the formula (4) may include a TEV domain. When the TEV domain is included in the amino acid sequence represented by r, R and $R^2$ can be separated by cleavage by the TEV protease. Moreover, the TEV domain is a preferable sequence for obtaining the effects of the present invention (that is, an increase in the amount of immobilization on a carrier, and an increase in immunoglobulin retention capability of the carrier). The amino acid sequence represented by r may include a mutant TEV domain that has an identity of 70% or more, and preferably 90% or more with the amino acid sequence of the TEV domain (irrespective of whether or not it can be cleaved by the TEV protease).

The number of amino acids included in the amino acid sequence represented by $R^1$ in the formula (4) is preferably 4 to 25, and the number of histidine residues included in the site including consecutive histidine residues in $R^1$ is preferably 4 to 8. The number of amino acids included in the amino acid sequence represented by r is preferably 10 to 50.

It is preferable that either or both of the amino acid sequence represented by R and the amino acid sequence represented by $R^2$ in the formula (3) include a domain t consisting of 1 to 50 amino acids and containing one amino acid selected from lysine, arginine, and cysteine. In this case, the amino acid sequence may include plural, the same or different domain t.

When protein 2 is used as a ligand for the filler for affinity chromatography of the present invention, it has high resistance to washing under alkali condition (for example, washing using an alkali solution of, for example, sodium hydroxide). It may be due to the fact that, by adding a consecutive histidine unit to Z domain, binding position between the porous particle and Z domain is changed from that without the consecutive histidine units, and alkali resistance is enhanced according to a certain structural change in Z domain after immobilization. Although actual reason was not determined by experiments, results of alkali resistance test indicate that a certain effect is obtained by addition of consecutive histidine units.

Furthermore, immunoglobulins are preferably isolated by using the filler for affinity chromatography of the present invention via the following processes: a process of adsorbing immunoglobulins onto the filler using the filler for affinity chromatography of the present invention (the first process); and a process for eluting the immunoglobulins for isolating immunoglobulins (the second process). Furthermore, carrying out the process of CIP washing the filler by using an alkali liquid (the third process) is preferable.

According to the first process, a solution containing immunoglobulins is applied into, for example, a column packed with the filler for affinity chromatography under the condition preferable for adsorption of the immunoglobulins onto the ligand of the filler. As used herein, the solution containing immunoglobulins may be any kind of solution containing immunoglobulins, and examples thereof include samples derived from a living organism such as blood serum, and supernatant of hybridoma culture. Condition for adsorption of immunoglobulins include immunoglobulin concentration of 0.1 to 10 g/L, solution pH of 5 to 9, column retention time of 0.5 to 50 minutes, and temperature of 0 to 40° C.

According to the first process, most of substances other than the immunoglobulins in solution pass through the column without being adsorbed. In general, in order to remove the substances that are weakly bound, the filler is washed by using a neutral buffer solution containing salts such as NaCl, for example, sodium dihydrogen phosphate/disodium hydrogen phosphate solution, citric acid/disodium hydrogen phosphate solution, hydrochloric acid/tris(hydroxymethyl)aminomethane solution, and HEPES/sodium hydroxide solution. According to the second process, an appropriate buffer solution with pH of 2 to 5, for example citric acid/sodium citrate solution, acetic acid/sodium acetate solution, and hydrochloric acid/glycine solution, is applied in order to elute the immunoglobulins. According to the third process, the filler is washed with an alkali solution (CIP washing).

Examples of the alkali solution used in the present invention include aqueous solution of sodium hydroxide, aqueous solution of potassium hydroxide, triethylamine, and tetrabutyl ammonium hydroxide.

1.2.5. Production of Protein 1 or 2

The protein 1 or 2 may be produced by publicly known gene recombination techniques such as those described in, for example, Frederick M. Ausbel et al., Current Protocols In Molecular Biology, Sambrook et al. (editor), Molecular Cloning (Cold Spring Harbor Laboratory Press, 3rd edition, 2001). For example, the protein 1 or 2 used in the present invention may be produced by the gene recombination technology disclosed in U.S. Pat. No. 5,151,350 specification. Specifically, an expression vector that includes a nucleic acid sequence that encodes the modified target protein (protein 1 or 2) is introduced into host cells (e.g., *Escherichia coli*) for transformation, and the cells are cultured in an appropriate liquid medium. Accordingly, a large amount of protein 1 or 2 that are used in the present invention can be economically obtained from the cultured cells. Examples of a preferable expression vector include publicly known vectors that can be replicated in bacteria. For example, the plasmid disclosed in U.S. Pat. No. 5,151,350, the plasmid disclosed in Sambrook et al. (editor), Molecular Cloning (Cold Spring Harbor Laboratory Press, 3rd edition, 2001) may be used. Publicly known method known to a person skilled in the art may be employed for transformation of a host by introducing a nucleic acid into the host. For example, the method disclosed in Sambrook et al. (editor), Molecular Cloning (Cold Spring Harbor Laboratory Press, 3rd edition, 2001) may be used. A method for culturing transformed bacteria and isolating the expressed proteins is well known to a person skilled in the art.

Specifically, the target expression vector can be obtained by synthesizing a DNA that encodes the desired amino acid sequence as separately synthesized oligonucleotides that include several tens of bases, binding these separated oligonucleotides by ligation reaction using a DNA ligase, and inserting it into a plasmid. In this case, a nucleic acid sequence using optimum codons of *Escherichia coli* is normally employed by a person skilled in the art so that the protein is efficiently expressed in *Escherichia coli*. It is also possible to construct a DNA sequence that encodes the desired amino acid sequence from the *Straphylococcus aureus* genomic DNA by the polymerase chain reaction (PCR).

For example, a nucleic acid used for the above mentioned production method may encode the immunoglobulin binding protein (protein 1 or 2) or a functional equivalent mutant thereof. The term "functional equivalent" of an immunoglobulin binding protein used herein refers to an immunoglobulin binding protein which has been modified (mutated) by, for example, addition, deletion, or substitution of an amino acid, chemical modification of an amino acid residue, which includes an amino acid sequence having an identity of 70% or more, and preferably 90% or more, with the amino acid sequence of the non-modified immunoglobulin binding protein, and which may be uses as an alternative to the non-modified immunoglobulin binding protein showing equivalent immunoglobulin binding activity. In other words, nucleic acids encoding the protein 1 or protein 2 are also included in the nucleic acid described above.

The protein 1 or 2 used in the present invention may be, as described above, a protein that includes one or more (preferably 2 to 12, and more preferably 4 to 10) immunoglobulin-binding domains. A cDNA that encodes such a protein may be easily obtained by tandemly linking a certain number of complementary DNA (cDNA) encoding a single immunoglobulin-binding domain. A protein that includes one or more immunoglobulin-binding domains can be easily produced by inserting the resulting cDNA into an appropriate expression plasmid.

For example, a protein having an amino acid sequence of SEQ ID NO: 4 (SPATK), or a protein having an amino acid sequence of SEQ ID NO: 2 (SP4Z), or a protein having an amino acid sequence of SEQ ID NO: 2 and SEQ ID NO: 4, in which one or more amino acids are deleted, substituted, or added, as well as having an immunoglobulin binding activity may preferably be used as the immunoglobulin binding protein used in the present invention.

1.2.6. Binding of Ligand

The method for binding the carrier to the ligand is preferably the method of using epoxy group included in the porous particle itself as a ligand binding site because it is a simple process. Furthermore, the method comprising activation of alcoholic hydroxyl group produced by ring opening of the epoxy group included in the porous particles using, for example, tosyl group, and binding the ligand to the porous particles, or the method of comprising forming a linker that extends from the epoxy group included in the porous particles or a group produced by ring opening of the epoxy group, and binding the ligand to the porous particles via the linker.

Condition for ligand binding varies depending on content amount of epoxy group in the porous particles before ligand binding and type of a ligand, a method well known to a person skilled in the art may be employed. When the ligand is a protein, an amino group at N terminal of the protein, or lysine and cysteine residues included in the protein can be used as a reaction point with epoxy group. When binding with a protein is desired, a protein as a ligand can be bound thereto by using an aqueous solution such as buffers having isoelectric point close to the protein, adding a salt such as sodium chloride and sodium sulfate, if necessary, and reacting the protein and porous particles under mixing for 1 to 24 hours at 0 to 40° C.

The amount of binding ligand is appropriately adjusted by selecting, for example, the type of ligand and type of target molecule. When an antibody binding protein such as protein A is to be bound as a ligand, the amount is preferably 10 to 200 mg, and more preferably 25 to 100 mg per 1 g of the porous particles. When an antibody binding protein such as protein A is to be bound as a ligand, when the ligand binding amount per 1 g of the porous particles is more than 10 mg or more, preferable dynamic binding capacity can be obtained, while, when 200 mg or less, the amount of liquid for eluting the bound antibody becomes appropriate.

1.2.7. Ring-Opened Epoxy Group

The ligand-bound porous particle constituting the filler for affinity chromatography of the present invention has ring-opened epoxy groups. The ring-opened epoxy groups are obtained by, after binding the ligand to the porous particles consisting of the above specific polymer, ring opening of epoxy groups included in the polymer (that is, ring opening of epoxy groups other than those bound to the ligand). This means that, before using the porous particles as a filler for affinity chromatography, substantially all of the epoxy groups on surface of the porous particles are ring-opened.

Furthermore, when substantially all of the epoxy groups on surface of the porous particles are ring-opened, it means that the amount of the epoxy groups remained on the ligand-bound porous particles having ring-opened epoxy groups is preferably less than 0.04 mmol/g, and more preferably less than 0.02 mmol/g. Most preferably, no epoxy groups are remained. When the remaining amount of the ring-opened epoxy groups is less than 0.04 mmol/g, preferable storage stability is obtained.

The alcoholic hydroxyl groups produced by ring opening of the epoxy group impart hydrophilicity to the surface of the particle, which can prevent, for example, non-specific adsorption of proteins, and which improves the toughness of the particles in water to prevent breakage of the particles at a high flow rate. The epoxy group included in the porous particle may be ring-opened by, for example, stirring the porous particles in aqueous solvent with heating or at room temperature in the presence of acid or alkali. The epoxy group may also be ring-opened by using a mercapto group-containing blocking agent like mercaptoethanol and thioglycerol or an amino group-containing blocking agent like monoethanolamine. The most preferred ring-opened epoxy groups are the ring-opened epoxy groups that are obtained by ring opening of epoxy groups contained in the porous particles by using thioglycerol. Using thioglycerol is advantageous in that, it is a raw material less toxic than mercaptoethanol, the ring-opened epoxy group bound to thioglycerol shows less non-specific adsorption than ring-opened groups obtained by using a blocking agent having an amino group, and it can improve the amount of dynamic binding.

1.2.8. Particle Size and Pore Volume

The ligand-bound porous particle having ring-opened epoxy groups, which constitute the filler for affinity chromatography of the present invention, preferably has a particle size of 35 to 100 μm, and more preferably 38 to 75 μm. When the particle size is 35 μm or more, preferable pressure characteristics are obtained. When the particle size is 100 μm or less, a filler having preferable dynamic binding capacity is obtained. Particle size of the ligand-bound porous particles having ring-opened epoxy groups may be adjusted by selecting the condition for polymerization of the porous particles as described above. Note that the "particle size" used herein refers to a volume average particle size determined using a laser diffraction/scattering particle size distribution analyzer.

The ligand-bound porous particle which have ring-opened epoxy groups for constituting the filler for affinity chromatography of the present invention preferably has a pore volume of 1.00 to 1.90 ml/g, and more preferably 1.05 to 1.85 ml/g, when pores having pore diameter within the range of 10 to 5,000 nm are measured using a mercury porosimeter. When the pore volume is within this range, a filler with a high dynamic binding capacity for proteins is obtained. In addition, when the pore volume is 1.90 ml/g or less, preferable pressure characteristics are obtained.

The ligand-bound porous particle which has ring-opened epoxy groups for constituting the filler for affinity chromatography of the present invention preferably has a specific surface area of 80 to 150 m$^2$/g, and more preferably 100 to 140 m$^2$/g. When the specific surface area is 80 m$^2$/g or more, a filler with a high dynamic binding capacity is obtained. When the specific surface area is 150 m$^2$/g or less, the filler has preferable strength and, due to prevention of degradation of the filler under high flow rate, increase of column pressure is prevented. Note that the "specific surface area" used herein refers to a value obtained by dividing the surface area of pores having a pore diameter of 10 to 5,000 nm determined using a mercury porosimeter by the dry weight of the particle.

The ligand-bound porous particle which has ring-opened epoxy groups for constituting the filler for affinity chromatography of the present invention preferably has a volume average pore diameter of 75 to 300 nm, and more preferably 80 to 250 nm. When the volume average pore diameter is 75 nm or more, decrease of the dynamic binding capacity at a high flow rate is prevented. When the volume average pore diameter is 300 nm or less, filler having preferable dynamic binding capacity is obtained irrespective of the flow rate. Note that the "volume average pore diameter" used herein refers to the volume average pore diameter of pores having a pore diameter of 10 to 5,000 nm determined using a mercury porosimeter.

When one particle of the ligand binding porous particle which has ring-opened epoxy groups for constituting the filler for affinity chromatography of the present invention is measured in wet state by micro hardness tester, the elastic modulus is preferably 3.0 to 10.0 MPa, more preferably 5.0 to 8.0 MPa. When the value is 3.0 MPa or more, preferable pressure characteristics are obtained. When the value is 10.0 MPa or less, a filler having preferable dynamic binding capacity for proteins is obtained. Note that the elastic modulus used herein refers to a value obtained by the step of dropping one drop of ligand binding porous particle having ring-opened epoxy groups for constituting the filler for affinity chromatography of the present invention in water slurry state is onto a stage of a micro hardness tester, pressing the one particle with the probe of a micro hardness tester from directly above the particle, measuring the stress (unit: N) when deformation of the particle to a degree of 5% of diameter is observed, and dividing the stress by the area (unit: $m^2$) of a circle having the same diameter as the particle size.

EXAMPLES

2. Examples

The filler for affinity chromatography relating to the embodiments of the present invention is further described below by way of examples. Note that the following examples generally illustrate aspects of the present invention, and the present invention is not limited to the following examples.

2.1. Evaluation Method 2.1.1. Epoxy Group Content

Epoxy group content in the porous particles before ligand binding was measured as follows: water dispersion of porous particles with exactly known mass concentration of about 10% were weighed and collected in a polyethylene bottle such that the mole number of epoxy groups that is calculated from the amount of monomers containing an epoxy group used for polymerization is 2.00 mmol, 25 mL of aqueous solution of calcium chloride with concentration of 38%, and 2.00 mL of 2 N hydrochloric acid were added thereto, the mixture was stirred at 75° C. for 2 hours and 30 minutes for ring opening of epoxy groups, 2.50 mL of 2 N hydrochloric acid was added for neutralization after cooling, and quantification was made by back titration with 0.1 N hydrochloric acid while monitoring the pH using a pH meter.

2.1.2. Particle Size

The volume average particle size of the particles was determined using a laser diffraction/scattering particle size distribution analyzer (trade name: LS13320, manufactured by Beckman Coulter, Inc.).

2.1.3. Pore Volume, Specific Surface Area, and Volume Average Pore Diameter

Particles were dried at 40° C. for 24 hours under vacuum to obtain dry particles, and the pore volume, specific surface area, and volume average pore diameter of the dry particles were determined using a mercury porosimeter (trade name: AutoPore IV9520, manufactured by Shimadzu Corporation). The measurement range was 10 to 5,000 nm (pore diameter).

2.1.4. Elastic Modulus

One drop of ligand-bound porous particles having ring-opened epoxy groups in water slurry state was placed on a stage of a micro hardness tester (trade name: HM2000, manufactured by Fischer Instruments K.K.), and then the stress (unit: N) was measured when the probe of a micro hardness tester is allowed to touch directly above the particle and the diameter of the particle is deformed by 5%. Furthermore, based on the graph of the position of the probe and stress, position of the probe at which stress=0 was calculated by least square method and the result was taken as the diameter of the particle tested. The stress recorded was divided by area (unit: $m^2$) of a circle having the same diameter as the diameter of the particle tested, and the result was taken as the elastic modulus of the particle measured. The measurement was carried out for arbitrarily selected five particles, and by obtaining average value of each elastic modulus, the elastic modulus of the ligand-bound porous particles having ring-opened epoxy groups which constitute the filler for affinity chromatography was obtained.

2.1.5. Dynamic Binding Capacity for Proteins

The dynamic binding capacity for a protein (human IgG antibody) was measured at a linear flow rate of 300 cm/hour using an instrument "AKTAprime plus" (manufactured by GE Healthcare Biosciences). The column volume was 4 mL (5 mmΦ×200 mm length). The human IgG antibody (trade name: HGG-1000, manufactured by Equitech Bio) was diluted to 5 mg/ml with a 20 mM phosphate buffer (pH: 7.5). The dynamic binding capacity was calculated from the adsorption amount of the human IgG antibody and the volume of the filler in column at an elution concentration of 10% (breakthrough). Herein below, dynamic binding capacity may be also referred to as DBC.

2.1.6. Pressure Characteristics

The filler consisting of the ligand-bound porous particles having ring-opened epoxy groups to be measured were packed in a column to have inner diameter of 16 mm and packing height of 100 mm. The column was then connected to AKTApilot manufactured by GE Healthcare Biosciences. When pure water was added while increasing gradually the linear flow rate by 50 cm/hour, the linear flow rate at which time dependent pressure increase over 0.05 MPa for one min during which pure water is supplied at constant linear flow rate was taken as compression flow rate. When no pressure increase was observed even at 3,000 cm/hour, the measurement was stopped and it was recorded as >3,000 cm/hour. Furthermore, when the absolute pressure of the column reaches 1.9 MPa and no further pressure increase is observed, the measurement was stopped and the linear flow rate at which it reached 1.9 MPa was recorded. The compression flow rate is preferably 900 cm/hour or more, more preferably 1200 cm/hour or more, still more preferably 1800 cm/hour or more, and most preferably 2700 cm/hour or more.

2.1.7. Binding Amount of Protein A

Binding amount of protein A (SPA) as a ligand bound to the porous particles was quantified by using a reagent kit using bicinchoninic acid (BCA) reagent. Specifically, 1 mg of the filler in terms of solid matter content was collected in a test tube and quantified by using BCA Protein Assay Kit manufactured by Thermo Fisher Scientific (formerly, PIERCE Company). The reaction was carried out by inversion mixing at 37° C. for 30 minutes. The calibration curve was established by using the same lot as protein A bound to the porous particles.

2.2. Test Example

2.2.1. Example 1

(i) Suspension Polymerization of Porous Particles 8.52 g of polyvinyl alcohol (trade name: PVA-217, manufactured by Kuraray Co., Ltd.), 2.13 g of sodium dodecyl sulfate (trade name: EAML 10 G, manufactured by Kao Corporation), and 4.26 g of sodium carbonate were added to 4091 g of purified water. The mixture was stirred overnight to prepare an aqueous solution (S-1-1). In addition, 30 g of (S-1-1) was set aside on the polymerization day, and to the remaining (S-1-1), 2.13 g of sodium nitrite was added and dissolved therein to prepare an aqueous solution (S-2-1).

Next, 125 g of glycerin dimethacrylate (manufactured by Shin-Nakamura Chemical Co., Ltd.), 17.9 g of glycidyl methacrylate (manufactured by Mitsubishi Rayon Co., Ltd.), and 35.9 g of glycerol monomethacrylate (manufactured by NOF CORPORATION) were dissolved in 86.4 g of 2-octanone (manufactured by Toyo Gosei Co., Ltd.) and 253 g of acetophenone (manufactured by Wako Pure Chemical Industries, Ltd.) to prepare a monomer solution. Furthermore, when the total mass of the monomers is 100 parts by mass, number of parts of each monomer is as follows: glycerin dimethacrylate 70 parts by mass, glycidyl methacrylate 10 parts by mass, and glycerol monomethacrylate 20 parts by mass.

To 30 g of (S-1-1), 2.2 g of 2,2'-azoisobutyronitrile (Wako Pure Chemical Industries, Ltd.) was added and dispersed to give initiator dispersion.

Next, the aqueous solution (S-2-1) prepared and the monomer solution were added to a 7 L separable flask equipped with a baffle, and after applying a thermometer, stirring blade, and a cooling tube, it was set in a hot-water bath and stirred by 220 rpm under nitrogen atmosphere. Subsequently, the separable flask was heated by a hot-water bath, and at the time point at which internal temperature reaches 85° C., the initiator dispersion was added and stirred for 5 hours while maintaining the temperature at 85° C.

After cooling, the reaction solution was filtered using a Nutsche and washed with pure water and isopropyl alcohol. The washed particles were transferred to a poly bottle, dispersed in water, and subjected to decantation for three times to remove small particles. According to the process, 12.5% by weight porous particle 1 dispersed in water was obtained (dry particle mass: 123 g). Epoxy group content in porous particle 1 was 0.47 mmol/g.

(ii) Ligand Production 2.2.1.1. Construction of SP4Z Expression Vector

The immunoglobulin binding protein (SP4Z) expression vector was constructed according to the following steps. FIG. 2 is a drawing for illustrating the method of constructing SP4Z vector.

(1) Step 1
By using DNA encoding monomer Z domain as a starting material, monomer Z domain vector (A-pETM11) (SP1Z) having NcoI restriction cleavage site and EcoRI restriction cleavage site was constructed.

(2) Step 2
Next, by adding one more Z domain to A-pETM11 vector, dimer Z domain vector (AB-pETM11) (SP2Z) having EcoRI restriction cleavage site and SacI restriction cleavage site was constructed.

(3) Step 3
Next, by adding still one more Z domain to AB-pETM11 vector, trimer Z domain vector (ABC-pETM11) (SP3Z) having SacI restriction cleavage site and Hind III restriction cleavage site was constructed.

(4) Step 4
Finally, by adding the fourth Z domain to ABC-pETM11 vector, pETM11-SP4Z vector having HindIII restriction cleavage site and XhoI restriction cleavage site was constructed.

2.2.1.2. Construction of SP1Z-pETM11 Vector (Monomer Z Domain Vector Having Terminal Codon)

By using SPZK DNA (SEQ ID NO: 3) as a template, primer 153 (SEQ ID NO: 5) as a forward primer, and primer 156 (SEQ ID NO: 8) as a reverse primer, PCR was carried out. The primer 153 and primer 156 include NcoI restriction cleavage site and SacI restriction enzyme cleavage site, respectively. PCR conditions are as follows.

Step 1: 94° C. for 1 minute 1 cycle, Step 2: 94° C. for 30 seconds, 55° C. for 30 seconds, 72° C. for 2.5 minutes (25 cycles), Step 3: 72° C. for 10 minutes 1 cycle, and after that, it was maintained at 4° C.

PCR product was purified by PCR purification by using a production kit manufactured by GE Healthcare Biosciences. Next, pETM11 vector digested by using NcoI restriction enzyme and SacI restriction enzyme was ligated to the PCR product. The digestion reaction by using the restriction enzyme was carried out for 1 hour at 37° C. using NcoI restriction enzyme and SacI restriction enzyme manufactured by New England Biolabs, and it was then subjected to PCR purification by using a production kit manufactured by GE Healthcare Biosciences.

Ligation was carried out overnight at room temperature by using T4 DNA ligase (manufactured by Invitrogen). The vector obtained after ligation was transformed into DH5a competent cell (manufactured by Biomedical Life Science) and the obtained transformants were cultured overnight at 37° C. in a LB medium containing kanamycin. From the positive colonies, plasmid was extracted and those having correct sequence of inserted DNA fragment were identified with 3730 DNA Sequencer (manufactured by Applied Biosystems).

2.2.1.3. Construction of A-pETM11 Vector (Monomer Z Domain Vector Without Termination Codon)

A-pETM11 vector was constructed in the same manner as the experiment 2.2.1.2. by using primer 153 as a forward primer and primer 154 (SEQ ID NO: 6) as a reverse primer instead of primer 153 and 156. In addition, for insertion of a DNA fragment, NcoI restriction cleavage site and EcoRI restriction cleavage site in pETM11 were utilized.

2.2.1.4. Construction of SP2Z-pETM11 Vector (Dimer Z Domain Vector Having Termination Codon)

It was constructed in the same manner as the experiment 2.2.1.2. by using primer 155 (SEQ ID NO: 7) as a forward primer and primer 156 as a reverse primer, producing the DNA of monomer Z domain having a EcoRI restriction cleavage site and a SacI restriction cleavage site by PCR, and inserting it to EcoRI restriction cleavage site and SacI restriction cleavage site of A-pETM11.

2.2.1.5. Construction of AB-pETM11 Vector (Dimer Z Domain Vector without Termination Codon)

AB-pETM11 vector was constructed in the same manner as the experiment 2.2.1.2. by using primer 155 as a forward primer and primer 157 (SEQ ID NO: 9) as a reverse primer, producing the DNA of monomer Z domain having a EcoRI restriction cleavage site and a SacI restriction cleavage site but no termination codon by PCR, and inserting it to EcoRI restriction cleavage site and SacI restriction cleavage site of A-pETM11.

2.2.1.6. Construction of SP3Z-pETM11 Vector (Trimer Z Domain Vector Having Termination Codon)

It was constructed in the same manner as the experiment 2.2.1.2. by using primer 158 (SEQ ID NO: 10) as a forward primer and primer 161 (SEQ ID NO: 13) as a reverse primer, producing the DNA of monomer Z domain having a SacI restriction cleavage site and XhoI restriction cleavage site by PCR, and inserting it to EcoRI restriction cleavage site and SacI restriction cleavage site of AB-pETM11.

2.2.1.7. Construction of ABC-pETM11 Vector (Trimer Z Domain Vector without Termination Codon)

ABC-pETM11 vector was constructed in the same manner as the experiment 2.2.1.2. by using primer 158 as a forward primer and primer 159 (SEQ ID NO: 11) as a reverse primer, producing the DNA of monomer Z domain having a SacI restriction cleavage site and HindIII restriction cleavage site but no termination codon by PCR, and inserting it to SacI restriction cleavage site and HindIII restriction cleavage site of AB-pETM11.

2.2.1.8. Construction of SP4Z-pETM11 Vector (Tetramer Z Domain Vector Having Termination Codon)

SP4Z-pETM11 vector was constructed in the same manner as the experiment 2.2.1.2. by using primer 160 (SEQ ID NO: 12) and primer 161, producing the DNA of monomer Z domain having a HindIII restriction cleavage site and XhoI restriction cleavage site by PCR, and inserting it to HindIII restriction cleavage site and XhoI restriction cleavage site of ABC-pETM11.

2.2.1.9. Expression and Purification of SP4Z

SP4Z-pETM11 vector obtained from above was added to E. coli (BL21) cells (manufactured by STRATAGENE) followed by addition of 1 mM IPTG (manufactured by Sigma-Aldrich) at 18° C., and a recombinant immunoglobulin binding protein (SP4Z) was expressed by incubation for 15 hours. The cells were incubated at 37° C. before induction until the absorbance (OD600) reached about 0.6. The cells were collected after the protein had been expressed, and lysed in a Tris buffer (pH: 8.0).

The resulting recombinant immunoglobulin binding protein (SP4Z) was purified by Ni affinity chromatography (Ni-NTA (nitrilotriacetic acid) particles manufactured by Qiagen). The purified immunoglobulin binding protein was further purified by anion exchange chromatography (Q-sepharose FF manufactured by GE Healthcare Biosciences). Purity of the immunoglobulin binding protein was 96% as confirmed by SDS-PAGE.

It was confirmed by MALDI-TOF mass spectrum analysis that the recombinant immunoglobulin binding protein (SP4Z) had the amino acid sequence (SEQ ID NO: 2) shown in FIG. 1 based on sequence match of each amino acid.

Furthermore, in FIG. 1, R and $R^2$ respectively correspond to R and $R^2$ in the formula (1) and (3), $R^1$ and r respectively correspond to $R^1$ and r in the formula (2) and (4). Furthermore, an underline in r indicates a TEV domain (TEV protease (peptide bond hydrolase) cleavage site).

(iii) Binding of Porous Particles to Ligand

A mixture solution in which 1 g of the porous particle 1 in terms of dry particle mass and 0.1 g of SP4Z are dispersed in 25 mL of 0.1 M phosphate buffer (pH 6.8) was prepared and mixed by inversion for 24 hours at 10° C. so that SP4Z can bind to the porous particle 1. The particles produced were filtered, mixed with 1 M thioglycerol (25 mL), and reacted for 4 hours at 30° C. for ring opening of remaining epoxy groups. After washing with PBS/0.5% Tween20 followed by PBS, filler for affinity chromatography 1 (A-1) consisting of ligand-bound porous particles having ring-opened epoxy groups was obtained. As a result of quantitative measurement using Thermo Scientific Pierce BCA Protein Assay kit, the amount of SP4Z bound to the particles was 41 mg/g of particle. The results are shown in Table 2.

(iv) Evaluation

Particle size of (A-1) was 54 μm, pore volume was 1.26 mL/g, specific surface area was 111 $m^2$/g, and volume average particle size was 101 nm. The elastic modulus was 5.6 MPa. Dynamic binding capacity for the protein (human IgG antibody) was 40 mg/mL and the pressure flow rate was 2,700 cm/hour.

2.2.2. Example 2

Filler for affinity chromatography 2 (A-2) consisting of ligand-bound porous particles having ring-opened epoxy groups was obtained in the same manner as the suspension polymerization of the Example 1 except that the porous particle 2 was prepared with the revolution number of 300 rpm. The filler was then evaluated. The results are shown in Table 2. Content of epoxy groups in the porous particle 2 was 0.45 mmol/g. Particle size of the porous particle 2 was 31 μm, pore volume was 1.438 mL/g, specific surface area was 132 $m^2$/g, and volume average particle size was 110 nm. The elastic modulus was 6.4 MPa. Dynamic binding capacity for the protein (human IgG antibody) was 40 mg/mL and the pressure flow rate was 1,100 cm/hour.

2.2.3. Example 3

(i) Suspension Polymerization of Porous Particles 0.600 g of polyvinyl alcohol (trade name: PVA-217, manufactured by Kuraray Co., Ltd.), 0.030 g of sodium dodecyl sulfate (trade name: EAML 10 G, manufactured by Kao Corporation), and 1.50 g of sodium sulfate were added to 300 g of purified water. The mixture was stirred overnight to prepare an aqueous solution (S-1-2). In addition, 5 g of (S-1-2) was set aside on the polymerization day, and to the remaining (S-1-2), 0.150 g of sodium nitrite was added and dissolved therein to prepare an aqueous solution (S-2-2).

Next, 8.19 g of glycerin dimethacrylate (manufactured by Shin-Nakamura Chemical Co., Ltd.) and 3.51 g of glycidyl methacrylate (manufactured by Mitsubishi Rayon Co., Ltd.) were dissolved in 6.25 g of 2-octanone (manufactured by Toyo Gosei Co., Ltd.) and 18.3 g of acetophenone (manufactured by Wako Pure Chemical Industries, Ltd.) to prepare a monomer solution. Furthermore, when the total mass of the monomers is 100 parts by mass, number of parts of each monomer is as follows: glycerin dimethacrylate 70 parts by mass and glycidyl methacrylate 30 parts by mass.

To 5 g of (S-1-2), 0.149 g of 2,2'-azoisobutyronitrile (Wako Pure Chemical Industries, Ltd.) was added and dispersed to give initiator dispersion.

Next, the aqueous solution (S-2-2) prepared and the monomer solution were added to a 0.5 L separable flask equipped with a baffle, and after applying a thermometer, stirring blade, and a cooling tube, it was set in a hot-water bath and stirred by 680 rpm under nitrogen atmosphere. Subsequently, the separable flask was heated by a hot-water bath, and at the time point at which internal temperature reaches 85° C., the initiator dispersion was added and stirred for 5 hours while maintaining the temperature at 85° C.

After cooling, the reaction solution was filtered using a Nutsche and washed with pure water and isopropyl alcohol. The washed particles were transferred to a poly bottle, dispersed in water, and subjected to decantation for three times to remove small particles. According to the process, 12.5% by weight porous particle 3 dispersed in water was obtained (dry particle mass: 8.7 g). Content of epoxy group in porous particle 3 was 1.7 mmol/g.

(ii) Ligand Production

Figure 3:
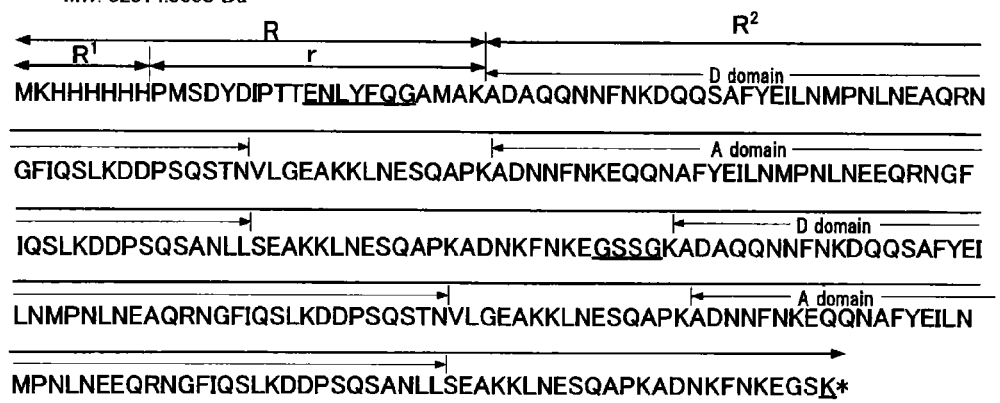
FIG. 3 is a diagram illustrating the amino acid sequence of the immunoglobulin binding protein (SPATK) prepared in Example 2 of the present invention.
Figure 4:
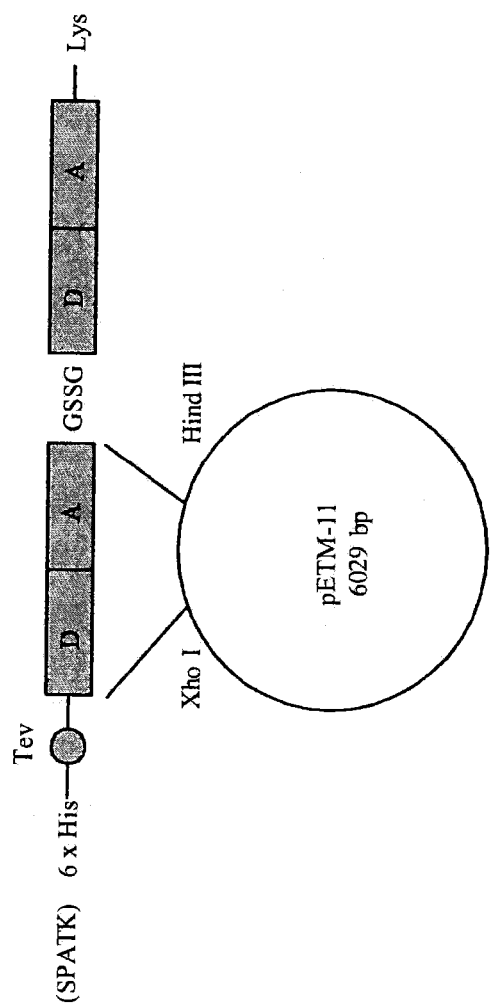
FIG. 4 is a diagram explaining the constitution of a DNA fragment that encodes the immunoglobulin binding protein related to Example 2 of the present invention and is inserted into an expression vector (pETM-11).

The immunoglobulin binding protein (SPATK (SEQ ID NO: 4)) having the amino acid sequence shown in FIG. 3 was prepared according to the preparation example (1) to (5).

(1) Step 1

By using genomic DNA of *Staphylococus aureus* as a template and primer (primer 11) having restriction enzyme NcoI site and primer (primer 12) having BamHI and HindIII site, a DNA encoding D-A domain was obtained by PCR. The resulting DNA was digested with the restriction enzyme NcoI and HindIII, and ligated to pETM11 which has been similarly digested with the restriction enzyme NcoI and HindIII to construct the SPAK plasmid.

(2) Step 2

By using SPAK plasmid as a template and primer (primer 13) having restriction enzyme BamHI site and primer (primer 14) having restriction enzyme HindIII site, a DNA encoding new D-A domain was obtained by PCR. The resulting DNA was digested with the restriction enzyme BamHI and HindIII, and ligated to SPAK plasmid which has been similarly digested with the restriction enzyme BamHI and HindIII to construct the SPATK plasmid.

(3) Construction of SPAK Plasmid

By using genomic DNA of *Staphylococus aureus* as a template and primer 11 and primer 12, PCR was carried out. Conditions for PCR were as follows.

Step 1: 94° C. for 1 minute 1 cycle, Step 2: 94° C. for 30 seconds, 53° C. for 30 seconds, 72° C. for 2.5 minutes (25 cycles), Step 3: 72° C. for 10 minutes 1 cycle, and after that, it was maintained at 4° C.

PCR product was purified by using a production kit manufactured by GE Healthcare Biosciences. Next, it was digested by using NcoI restriction enzyme and HindIII restriction enzyme. pETM11 vector was similarly digested by using NcoI restriction enzyme and HindIII restriction enzyme. The digestion reaction by using the restriction enzyme was carried out by using NcoI restriction enzyme and HindIII restriction enzyme manufactured by New England Biolabs, and it was then subjected to purification by using a production kit manufactured by GE Healthcare Biosciences. Ligation was carried out overnight at room temperature by using T4 DNA ligase (manufactured by Invitrogen). The vector obtained after ligation was transformed into DH5a competent cell (manufactured by Biomedical Life Science). From the positive colonies, plasmids having correct sequence (SPAK plasmid) were identified with 3730 DNA Sequencer (manufactured by Applied Biosystems).

(4) Construction of SPATK Plasmid

By using SPAK plasmid as a template and primer 13 and primer 14, a DNA encoding new D-A domain was obtained by PCR. Conditions for PCR were as follows. Step 1: 94° C. for 1 minute 1 cycle, Step 2: 94° C. for 30 seconds, 55° C. for 30 seconds, 72° C. for 2.5 minutes (25 cycles), Step 3: 72° C. for 10 minutes 1 cycle, and after that, it was maintained at 4° C. PCR product was purified by using a production kit manufactured by GE Healthcare Biosciences. Next, the DNA was digested by using BamHI restriction enzyme and HindIII restriction enzyme. SPAK plasmid was similarly digested by using BamHI restriction enzyme and HindIII restriction enzyme. The digestion reaction by using the restriction enzyme was carried out by using BamHI restriction enzyme and HindIII restriction enzyme manufactured by New England Biolabs, and it was then subjected to purification by using a production kit manufactured by GE Healthcare Biosciences. The ligation reaction was carried overnight at room temperature by using T4 DNA ligase (manufactured by Invitrogen). The vector obtained after ligation was transformed into DH5a competent cell (manufactured by Biomedical Life Science). From the positive colonies, plasmids having correct sequence (SPATK plasmid) were identified with 3730 DNA Sequencer (manufactured by Applied Biosystems).

(5) Expression and Purification of SPATK

SPATK plasmid obtained from above was transformed into *E. coli* (BL21) cells (manufactured by STRATAGENE) followed by addition of 1 mM IPTG (manufactured by Sigma-Aldrich) at 18° C., and a recombinant immunoglobulin binding protein (SPATK) was expressed by incubation for 15 hours. The cells were incubated at 37° C. before induction until the absorbance (OD600) reached about 0.6. The cells were collected after the protein had been expressed, and lysed in a Tris buffer (pH: 8.0).

The resulting recombinant immunoglobulin binding protein (SPATK) was purified by Ni affinity chromatography (Ni-NTA (nitrilotriacetic acid) particles manufactured by Qiagen). The purified immunoglobulin binding protein was further purified by anion exchange chromatography (Q-Sepharose FF manufactured by GE Healthcare Biosciences). Purity of the immunoglobulin binding protein was 96% as confirmed by SDS-PAGE.

It was confirmed by MALDI-TOF mass spectrum analysis that the recombinant immunoglobulin binding protein (SPATK) had the amino acid sequence shown in FIG. 3 based on sequence match of each amino acid.

TABLE 1

| Primer name | Sequence |
| --- | --- |
| Primer11 | 5'-CAT GCC ATG GCG AAA GCT GAT GCG CAA CAA AAT |

TABLE 1-continued

| Primer name | Sequence |
|---|---|
| Primer12 | 5'-CCC AAG CTT TTA CTT GGA TCC TTC TTT GTT GAA TTT GTT ATC CG |
| Primer13 | 5'-CGG GGA TCC TCA GGC AAA GCT GAT GCG CAA CAA AAT |
| Primer14 | 5'-CCC AAG CTT TTA CTT CGA CCC TTC TTT GTT GAA TTT GTT ATC CG |

(iii) Binding of Porous Particles to Ligand

A mixture solution in which 1 g of the porous particle 3 in terms of dry particle mass and 0.1 g of SPATK are dispersed in 25 mL of 0.1 M phosphate buffer (pH 6.8) was prepared and mixed by inversion for 24 hours at 10° C. so that SPATK can bind to the porous particle 3. The particles produced were filtered, mixed with 1 M thioglycerol (25 mL), and reacted for 4 hours at 30° C. for ring opening of remaining epoxy groups. After washing with PBS/0.5% Tween20 followed by PBS, filler for affinity chromatography 3 (A-3) consisting of ligand-bound porous particles having ring-opened epoxy groups was obtained. As a result of quantitative measurement using Thermo Scientific Pierce BCA Protein Assay kit, the amount of SPATK bound to the particles was 44 mg/g of particle. The results are shown in Table 2.

(iv) Evaluation

Particle size of (A-3) was 50 μm, pore volume was 1.07 mL/g, specific surface area was 104 $m^2/g$, and volume average particle size was 68 nm. The elastic modulus was 6.6 MPa. Dynamic binding capacity for the protein (human IgG antibody) was 39 mg/mL and the pressure flow rate was >3000.

2.2.4. Examples 4 to 6

Filler 4 to 6 (A-4 to A-6) for affinity chromatography consisting of ligand-bound porous particles having ring-opened epoxy groups was obtained in the same manner as the Example 3 except that, when the total mass of the monomers is 100 parts by mass, the number of parts of each monomer was changed to those shown in Table 2. The filler was then evaluated. The results are shown in Table 2.

2.2.5. Example 7

Filler 7 (A-7) for affinity chromatography consisting of ligand-bound porous particles having ring-opened epoxy groups was obtained in the same manner as the suspension polymerization of the Example 3, except that 1.50 g of sodium nitrite was used instead of sodium sulfate and, when total mass of the monomers is 100 parts by mass, the number of parts of each monomer was changed to those shown in Table 2. The filler was then evaluated. The results are shown in Table 2.

2.2.6. Comparative Example 1 and 2

Fillers 1 and 2 (B-1 and B-2) for affinity chromatography 1 and 2 consisting of ligand-bound porous particles having ring-opened epoxy groups was obtained in the same manner as the Example 3 except that, when total mass of the monomers is 100 parts by mass, number of parts of each monomer was changed to those shown in Table 3. The filler was then evaluated. The results are shown in Table 3.

2.2.7. Example 8

(i) Suspension Polymerization of Porous Particles 8.51 g of polyvinyl alcohol (trade name: PVA-217, manufactured by Kuraray Co., Ltd.), 0.425 g of sodium dodecyl sulfate (trade name: EAML 10 G, manufactured by Kao Corporation), and 21.3 g of sodium sulfate were added to 4257 g of purified water. The mixture was stirred overnight to prepare an aqueous solution (S-1-6). In addition, 20 g of (S-1-6) was set aside on the polymerization day, and to the remaining (S-1-6), 2.13 g of potassium iodide was added and dissolved therein to prepare an aqueous solution (S-2-6).

Next, 104 g of monomer consisting of 60% by mass of pentaerythritol triacrylate and 40% by mass of pentaerythritol tetraacrylate (trade name: NK ester A-TMM-3LM-N, manufactured by Shin-Nakamura Chemical Co., Ltd.), 20.7 g of 4-hydroxybutylacrylate glycidyl ether (manufactured by Nippon Kasei Chemical Co., Ltd.), and 82.9 g of hydroxyethylacrylamide (manufactured by Kohjin Co., Ltd.) were dissolved in 134 g of 2-octanone (manufactured by Toyo Gosei Co., Ltd.) and 169 g of acetophenone (manufactured by Wako Pure Chemical Industries, Ltd.) to prepare a monomer solution. Furthermore, when the total mass of the monomers is 100 parts by mass, the number of parts of each monomer is as follows: pentaerythritol triacrylate 30 parts, pentaerythritol tetraacrylate 20 parts, 4-hydroxybutylacrylateglycidyl ether 10 parts, and hydroxyethylacrylamide 40 parts.

To 20 g of (S-1-6), 1.92 g of 2,2'-azoisobutyronitrile (Wako Pure Chemical Industries, Ltd.) was added and dispersed to give initiator dispersion.

Next, the aqueous solution (S-2-6) prepared and the monomer solution were added to a 7 L separable flask equipped with a baffle, and after applying a thermometer, stirring blade, and a cooling tube, it was set in a hot-water bath and stirred by 300 rpm under nitrogen atmosphere. Subsequently, the separable flask was heated by a hot-water bath, and at the time point at which internal temperature reaches 80° C., the initiator dispersion was added and stirred for 5 hours while maintaining the temperature at 80° C.

After cooling, the reaction solution was filtered using a Nutsche and washed with pure water and isopropyl alcohol. The washed particles were transferred to a poly bottle, dispersed in water, and subjected to decantation for three times to remove small particles. According to the process, 12.5% by weight porous particle 8 dispersed in water was obtained (dry particle mass: 107 g). Content of epoxy group in porous particle 8 was 0.29 mmol/g.

(ii) Ligand Production, (iii) Binding of Porous Particles to Ligand, and (iv) Evaluation Production and evaluation were made in the same manner as the Example 1. The results are given in Table 4.

2.2.8. Example 9

Filler 9 (A-9) for affinity chromatography consisting of ligand-bound porous particles having ring-opened epoxy groups was obtained in the same manner as the suspension polymerization of the Example 8, except that 96.7 g of monomer consisting of 60% by mass of pentaerythritol triacrylate and 40% by mass of pentaerythritol tetraacrylate (trade name: NK ester A-TMM-3LM-N, manufactured by Shin-Nakamura Chemical Co., Ltd.), 19.3 g of 4-hydroxybutylacrylate glycidyl ether (manufactured by Nippon Kasei Chemical Co., Ltd.), and 77.3 g of hydroxyethylacrylamide (manufactured by Kohjin Co., Ltd.) were dissolved in 139 g of 2-octanone (manufactured by Toyo Gosei Co., Ltd.) and 175 g of acetophenone (manufactured by Wako Pure Chemical Industries, Ltd.) to prepare a monomer solution and the mass of 2,2'-azoisobutyronitrile (Wako Pure Chemical Industries, Ltd.) was changed to 2.69 g. The filler was then evaluated. The results are shown in Table 4.

2.2.9. Example 10

Filler 10 (A-10) for affinity chromatography consisting of ligand-bound porous particles having ring-opened epoxy groups was obtained in the same manner as the Example 9 except that, at the time point at which internal temperature reaches 85° C., initiator dispersion was added and stirring was carried out for 5 hours while maintaining the temperature at 85 to 90° C. The filler was then evaluated. The results are shown in Table 4.

TABLE 2

| | X-1 GLDM | M-1 GMA | M-2 GLM | Content of epoxy group mmol/g | Particle size μm | Pore volume mL/g | Specific surface area m$^2$/g | Pore diameter nm | Elastic modulus MPa | SPA binding amount mg/g | DBC mg/mL | Compression flow rate cm/hr |
|---|---|---|---|---|---|---|---|---|---|---|---|---|
| Example 1 | 70 | 10 | 20 | 0.47 | 54 | 1.26 | 111 | 101 | 5.6 | Z 41 | 40 | 2700 |
| Example 2 | 70 | 10 | 20 | 0.45 | 31 | 1.43 | 132 | 110 | 6.4 | Z 38 | 40 | 1100 |
| Example 3 | 70 | 30 | 0 | 1.7 | 50 | 1.07 | 104 | 68 | 6.6 | T 44 | 39 | >3000 |
| Example 4 | 80 | 20 | 0 | 1.1 | 49 | 1.09 | 105 | 70 | 7.0 | T 42 | 38 | >3000 |
| Example 5 | 90 | 10 | 0 | 0.62 | 53 | 1.06 | 104 | 68 | 8.5 | T 47 | 33 | >3000 |
| Example 6 | 95 | 5 | 0 | 0.31 | 55 | 1.03 | 103 | 63 | 13.6 | T 35 | 29 | >3000 |
| Example 7 | 70 | 10 | 20 | 0.24 | 38 | 0.98 | 103 | 53 | 6.0 | Z 59 | 27 | 1350 |

GLDM: glycerin dimethacrylate
GLM: glycerol monomethacrylate
GMA: glycidyl methacrylate Regarding the symbol given before the numerical value of SPA binding amount, "Z" represents binding of SP4A and "T" represents binding of SPATK.

TABLE 3

| | X-1 — | X-2 EDMA | M-1 GMA | Content of epoxy group mmol/g | Particle size μm | Pore volume mL/g | Specific surface area m$^2$/g | Pore diameter nm | Elastic modulus MPa | SPA binding amount mg/g | DBC mg/mL | Compression flow rate cm/hr |
|---|---|---|---|---|---|---|---|---|---|---|---|---|
| Comparative Example 1 | 0 | 80 | 20 | 1.2 | 48 | 1.32 | 104 | 121 | 7.5 | T 32 | 29 | >3000 |
| Comparative Example 2 | 0 | 90 | 10 | 0.63 | 48 | 1.32 | 104 | 123 | 7.7 | T 36 | 9 | >3000 |

EDMA: ethylene glycol dimethacrylate
GMA: glycidyl methacrylate

Regarding the symbol given before the numerical value of SPA binding amount, "Z" represents binding of SP4A and "T" represents binding of SPATK.

TABLE 4

| | X-1 PE3A | X-2 PE4A | M-1 HBAGE | M-2 HEAA | Content of epoxy group mmol/g | Particle size μm | Pore volume mL/g | Specific surface area m$^2$/g | Pore diameter nm | Elastic modulus MPa | SPA binding amount mg/g | DBC mg/mL | Compression flow rate cm/hr |
|---|---|---|---|---|---|---|---|---|---|---|---|---|---|
| Example 8 | 30 | 20 | 10 | 40 | 0.29 | 38 | 1.46 | 102 | 169 | 5.6 | Z 70 | 45 | 2250 |
| Example 9 | 30 | 20 | 10 | 40 | 0.28 | 41 | 1.58 | 101 | 221 | 3.4 | Z 64 | 43 | 2100 |
| Example 10 | 30 | 20 | 10 | 40 | 0.26 | 42 | 1.93 | 67 | 302 | 2.6 | Z 37 | 23 | 900 |

PE3A: pentaerythritol triacrylate
PE4A: pentaerythritol tetraacrylate
HBAGE: 4-hydroxybutylacrylate glycidyl ether
HEAA: hydroxyethylacrylamide Regarding the symbol given before the numerical value of SPA binding amount, "Z" represents binding of SP4A and "T" represents binding of SPATK.

According to Tables 2 to 4, it was found that retained ligand amount is higher and pressure characteristics are more favorable in the case in which the filler of the Examples 1 to 10 are used compared to the case in which the filler of the Comparative Examples 1 and 2 are used.

2.2.10. Comparative Example 3

A monomer solution was prepared in the same manner as the suspension polymerization of the Example 1, except that 142.9 g of glycidyl methacrylate was used instead of 125 g of glycerin dimethacrylate (manufactured by Shin-Nakamura Chemical Co., Ltd.) and 17.9 g of glycidyl methacrylate (manufactured by Mitsubishi Rayon Co., Ltd.) for carrying out the polymerization. Furthermore, when the total mass of the monomers is 100 parts by mass, number of parts of each monomer is as follows: glycidyl methacrylate 80 parts by mass and glycerol methacrylate 20 parts by mass. Subsequently, after cooling, the reaction solution was filtered using a Nutsche and an attempt was made to wash it with pure water and isopropyl alcohol. However, white lumps containing the solvent were formed during filtration to yield clogging, and therefore it was impossible to move on to the next process.

The embodiments according to the present invention have been described above. Note that the present invention is not limited to the above embodiments. Various modifications and variations may be made. The present invention includes various other configurations substantially the same as the configurations described in connection with the embodiments (such as a configuration having the same function, method, and results, or a configuration having the same objective and results). The present invention also includes a configuration in which a non-essential element described in connection with the above embodiments is replaced with another element. The present invention also includes a configuration having the same effects as those of the configurations described in connection with the above embodiments, or a configuration capable of achieving the same objective as that of the configurations described in connection with the above embodiments. The present invention also includes a configuration in which a known technique is added to the configurations described in connection with the above embodiments.

INDUSTRIAL APPLICABILITY

The filler for affinity chromatography of the present invention has higher retention amount of an immunoglobulin binding protein and an excellent property of retaining the protein compared to conventional carriers. Accordingly, a capturing amount of a target protein can be increased, and therefore binding capacity for the target protein (antibody) can be increased. As a result, the target compound with high purity can be obtained in a large amount with high efficiency and low cost.

---

The invention claimed is:

1. A filler comprising:
   (a) a porous particle consisting of a polymer of vinyl monomer comprising
      a cross-linkable vinyl monomer comprising a hydroxyl group but not an epoxy group and an epoxy group-containing non-cross-linkable vinyl monomer,
      or a cross-linkable vinyl monomer comprising a hydroxyl group and epoxy group,
   (b) a ligand bound to an epoxy group of the porous particle (a), and
   (c) a ring-opened epoxy group, obtained by ring-opening of the epoxy group contained in the polymer with thioglycerol,
   wherein the filler is suitable for affinity chromatography.

2. The filler according to claim 1, wherein the ligand (b) is a protein comprising at least one selected from the group consisting of a protein A, an immunoglobulin-binding domain of protein A, and a variant thereof.

3. The filler according to claim 1, wherein the vinyl monomer consists of:
   20 to 90 parts by mass of (X-1) a cross-linkable vinyl monomer comprising a hydroxyl group but not an epoxy group,
   0 to 40 parts by mass of (X-2) a cross-linkable vinyl monomer comprising neither a hydroxyl group nor an epoxy group,
   1 to 40 parts by mass of (M-1) an epoxy group-containing non-cross-linkable vinyl monomer, and
   0 to 70 parts by mass of (M-2) a non-cross-linkable vinyl monomer that does not contain epoxy group,
   with the proviso that the total amount of (X-1), (X-2), (M-1) and (M-2) is 100 parts by mass.

4. The filler according to claim 1, wherein the porous particle (a) is obtained by performing suspension polymerization of:
   100 parts by mass of the vinyl monomer, and
   a water-based mixture comprising (P-1) as an essential component, wherein the (P-1) is at least one porogen selected from the group consisting of a linear, branched or cyclic, C7 to C14 alcohol, an ether, an aldehyde, a ketone and an ester, and C8 to C10 alkylbenzene,
   with the proviso that the total amount of porogens is 100 to 400 parts by mass, and the content of (P-1) is 10% by mass or more in 100% by mass of the total amount of porogens.

5. The filler according to claim 1, wherein the pore volume of the porous particle (a) obtainable by measuring micropores having pore diameter in the range of 10 to 5,000 nm with a mercury porosimeter, is 1.00 to 1.90 ml/g.

6. The filler according to claim 1, wherein the particle size of the porous particle (a) is 35 to 100 μm.

7. A method for isolating immunoglobulins, the method comprising:
   absorbing immunoglobulins with the filler according to claim 1, wherein the ligand is protein A, protein G or an immunoglobulin binding protein; and
   eluting the immunoglobulins.

8. A packed column, which is packed with the filler according to claim 1.

* * * * *